US007358061B2

(12) United States Patent
Yamamoto et al.

(10) Patent No.: US 7,358,061 B2
(45) Date of Patent: Apr. 15, 2008

(54) METHODS OF DIAGNOSING THYROID CARCINOMA

(75) Inventors: Hiroshi Yamamoto, Osaka (JP);
Kazutake Tsujikawa, Hyogo (JP);
Yukiko Uchino, Osaka (JP); Noboru Konishi, Nara (JP)

(73) Assignee: Fuso PHarmaceutical Industries, Ltd., Osaka (JP)

( * ) Notice: Subject to any disclaimer, the term of this patent is extended or adjusted under 35 U.S.C. 154(b) by 470 days.

(21) Appl. No.: 10/945,772

(22) Filed: Sep. 21, 2004

(65) Prior Publication Data
US 2005/0042222 A1 Feb. 24, 2005

Related U.S. Application Data

(62) Division of application No. 09/719,272, filed as application No. PCT/JP99/03054 on Jun. 7, 1999, now Pat. No. 6,846,912.

(30) Foreign Application Priority Data
Jun. 8, 1998 (WO) ........................ PCT/JP98/02542

(51) Int. Cl.
G01N 33/574 (2006.01)
(52) U.S. Cl. ...................... 435/7.23; 435/7.1
(58) Field of Classification Search ............... None
See application file for complete search history.

(56) References Cited
U.S. PATENT DOCUMENTS

| 4,752,583 | A | 6/1988 | Jensen |
| 5,538,886 | A | 7/1996 | Schlessinger |
| 5,646,333 | A | 7/1997 | Dobres |
| 5,736,149 | A | 4/1998 | Avjioglu |
| 5,837,505 | A | 11/1998 | Della-Cioppa |
| 5,888,794 | A | 3/1999 | Schlessinger |
| 5,916,561 | A | 6/1999 | Adolf |

FOREIGN PATENT DOCUMENTS

EP 1 097 944 A1 5/2001

OTHER PUBLICATIONS

Brennan et al., J. Autoimmunity, 1989, 2 (suppl.): 177-186.*
Zimmer, Cell Motility and the Cytoskeleton, 1991. 20:325-337.*
Hell et al., Laboratory Investigation, 1995, 73: 492-496.*
Fu et al., EMBO J., 1996, 15:4392-4401.*
Vallejo et al., Biochimie, 2000 82:1129-1133.*
Jang et al., Clinical Exp. Metastasis, 1997, 15: 469-483.*
U.S. Appl. No. 09/743,492, Yamamoto et al.
Ahmad et al. "Functional Association Between the Insulin Receptor and the Transmembrane Protein-Tyrosine Phosphatase LAR in Intact Cells." *J Biol Chem.*, 272:448-57 (1997).
Ahmad et al. "Increased Abundance of the Receptor-Type Protein-Tyrosine Phosphatase LAR Accounts for the Elevated Insulin Receptor Dephosphorylating Activity in Adipose Tissue of Obese Human Subjects" *J Clin Invest.*, 95:2806-12 (1995).
Bendayan, M., "Possibilities of False Immunocytochemical Results Generated by The Use of Monoclonal Antibodies: The Example of the Anti-proinsulin Antibody," *J. Histochem. Cytochem.*, 43:881-86 (1995).
Besco et al., "Genomic Organization and Alternative Splicing of the Human and Mouse RPTPp Genes," *BMC Genomics*, 2:1-13 (2001).
Bost et al., "Antibodies against a peptide sequence within the HIV envelope protein crossreacts with human interleukin-2," Immunol. Invest., 17(6-7):577-86 (1988).
Debant, et al., "The Multidomain Protein Trio Binds the LAR transmembrane Tyrosine Phosphatase, Contains a Protein Kinase Domain, and has Separate rac-specific and rho-specific Guanine Nucleotide Exchange Factor Domains," *Proc. Natl. Acad. Sci. U.S.A.*, 93:5466-71 (1996).
Faure et al., "Diagnostic Features of Primary Malignant Lymphomas of the Thyroid with Monoclonal Antibodies," *Cancer(Phila)*, 61:1852-1861 (1988).
Fernando et al., "Antibodies to the Human 2 Subunit of the GABAa/Benzodiazepine Receptors," *J. Neurochem.*, 64:1305-1311 (1995).
Furukawa et al. "Specific Interaction of the CD45 Protein-Tyrosine Phosphatase with Tyrosine-Phosphorylated CD3 zeta Chain" *Proc Natl Acad Sci U S A.*, 91:10928-32 (1994).
Goldstein et al., "Regulation of Insulin Receptor Signaling by Protein-Tyrosine Dephosphorylation", *Receptor*, 3:1-15(1993).
Hersh, et al., "The Salmonella Invasin SipB Induces Macrophage Apoptosis by Binding to caspase-1," *Proc. Natl. Acad. Sci. U.S.A.*, 96:2396-401 (1999).
Itoh et al., "Purification and Characterization of the Catalytic Domains of the Human Receptor-linked Protein Tyrosine Phosphatases HPTPβ, Leukocyte Common Antigen (LCA), and Leukocyte Common Antigen-related Molecule (LAR)," *J. Biol. Chem.*, 267:12356-12363 (1992).
Kanemitsu, O., "Koutai Kougaku Nyuumon," K.K. Chijin Shokan, 145-166 (1994).
Streuli et al. "A New Member of the Immunoglobulin Superfamily that has a Cytoplasmic Region Homologous to the Leukocyte Common Antigen" *J Exp Med.*, 168:1523-30 (1988).
Streuli et al. "Distinct Functional Roles of the Two Intracellular Phosphatase Like Domains of the Receptor-linked Protein Tyrosine Phosphatases LCA and LAR," *EMBO J.*, 9:2399-407 (1990).
Streuli et al. "Expression of the Receptor-Linked Protein Tyrosine Phosphatase LAR: Proteolytic Cleavage and Shedding of the CAM-like Extracellular Region," *EMBO J.*, 11:897-907 (1992).
Supplemental European Search Report for EP 99 92 3958 dated Feb. 18, 2004.

(Continued)

*Primary Examiner*—Misook Yu
*Assistant Examiner*—Mark Halvorson
(74) *Attorney, Agent, or Firm*—Marshall, Gerstein & Borun LLP

(57) ABSTRACT

Antibodies to a LAR phosphatase subunit, particularly antibodies having specificity to an intracellular domain of a phosphatase subunit, methods for generation thereof and cells producing these antibodies, and determination and examination methods of LAR/LAR derived molecules using these antibodies, as well as uses of these antibodies in diagnosis and therapy of thyroid cancer are disclosed.

1 Claim, 14 Drawing Sheets

OTHER PUBLICATIONS

Takeuchi et al., "Characterization of AE-6 Monoclonal Antibody Recognizing VHCSAGV Sequence in CD45 PTPase Domain," *Tissue Antigens*, 42:441 (1993).

Yakura, "CD45 Isoforms and Functional Diversity of T and B Cells," *Med. Immunol.*, 27:333-339 (1994). (English translation of Table 1 of p. 334).

Yu et al., "The N-terminal and C-terminal Domains of a Receptor Tyrosine Phosphatase are Associated by Non-covalent Linkage," *Oncogene*, 7:1051-1057 (1992).

Zhang et al., "LAR Tyrosine Phosphatase Receptor: Alternative Splicing is Preferential to the Nervous System, Coordinated with Cell Growth and Generates Novel Isoforms Containing Extensive CAG Repeats," *J. Cell Biol.*, 128:415-431 (1995).

Zhang, et al., "Molecular Cloning and Expression of a Unique Receptor-Like Protein-Tyrosine-Phosphatase in the Leukocyte-Common-Antigen-Related Phosphatase Family," Biochem J., 302:39-47 (1994).

* cited by examiner

METHODS OF DIAGNOSING THYROID CARCINOMA

This application is a division of U.S. application Ser. No. 09/719,272, which was the National Stage of International Application No. PCT/JP99/03054, filed Jun. 7, 1999.

FIELD OF THE INVENTION

The present invention relates to antibodies that specifically bind to a P-subunit, i.e., a phosphatase subunit, of LAR (leukocyte antigen related) protein, and particularly relates to the antibodies that specifically bind to an intracellular domain of LAR, and to methods for generation thereof. More particularly, the present invention provides antibodies that are useful for analysis and quantitation of protein tyrosine phosphatases, identification and isolation of LAR-related molecules, and medical drugs applicable to treatments such as therapy, prevention and alleviation as well as diagnosis of the disease states associated with insulin resistance.

BACKGROUND OF THE INVENTION

Mechanisms involving in the onset of arteriosclerosis have been gradually elucidated in these days, and risk factors thereof have been identified. Especially, hypercholesterolemia, hypertension, diabetes, and smoking are recognized to be manifest four risk factors, thus the therapeutic treatments have been extensively carried out. Clinically common pathologies of these disease states are insulin resistance. The meaning of insulin resistance is nearly equivalent to the reduction of sensitivity to insulin in cells, thereby the actions of insulin upon the uptake of sugar into the cells are deteriorated. The insulin resistance may be caused due to the abnormalities in secretion of insulin itself, abnormalities of insulin receptors on target cells, abnormalities of an intracellular signaling system, and reduced supply of sugar to the tissue based on peripheral circulatory disorder that is caused hemodynamically. Reaven, 1988, reports that many pathological states are developed due to the insulin resistance, and designates a pathological state as "syndrome X" that may concurrently represent insulin resistance, glucose tolerance abnormalities, hyperinsulinemia, hypertriglyceridemia, hypo-HDL cholesterolemia and hypertension, and further suggests that the pathological state syndrome X closely participates in the onset of arteriosclerosis (Reaven, G. M. et al., *Diabetes*, 37, 1595-1607, 1988).

In addition, sugar supply to the cells is known to be generally decreased through insulin resistance, accompanied by enhancement of insulin secretion from pancreas, thus leading to hyperinsulinemia. Therefore, several problems in connection with insulin resistance have been raised in clinical fields. For example, insulin resistance and hyperinsulinemia are reported to promote-diabetic nephritis (Niskanen, L. et al., *Diabetes*, 41, 736-741, 1993), and to elevate frequency of diabetic retinopathy (Yip, J. et al., *Lancet*, 341, 369-370, 1993). Moreover, insulin resistance has been reported to enhance plasminogen activator inhibitor 1 (PAI-1), to deteriorate the functions of a blood fibrinolytic system (Potter van Loon B J et al., *Metab. Clin. Exp.*, 42, 945-954, 1993), and to trigger arterial atherosclerosis (Sato, Y. et al., *Diabetes*, 38, 91-96, 1989).

Prevalence rate of diabetes accounts for 5% of the total population, and approximately six millions of Japanese citizens are suffering from diabetes. Diabetes comprises insulin dependent diabetic mellitus (IDDM) and insulin independent diabetic mellitus (NIDDM). Reportedly, IDDM accounts for about 7% of the total diabetes cases, whilst NIDDM does about 90%. In particular, a significant causative factor of the onset of NIDDM that corresponds to a majority of diabetes has been conceived as the insulin resistance.

To date, tyrosine phosphorylation has been elucidated to play important roles in signal transduction of insulin. Insulin receptor is a hetero-tetramer of two glycoprotein subunits, namely an α-subunit having a molecular weight of 135 kDa and a β-subunit having a molecular weight of 95 kDa, which are bound through disulfide bonds resulting in α2β2 structure. The α-subunit has an insulin binding activity, while the β-subunit has a protein tyrosine kinase (PTK) domain that is activated by autophosphorylation. Accordingly, when insulin is bound to the α-chain of an insulin receptor, certain tyrosine residues existing in the β-chain of the insulin receptor are autophosphorylated. The activity of insulin receptor tyrosine kinase is further promoted through the tyrosine autophosphorylation. It is reported that thus activated insulin receptor tyrosine kinase phosphorylates tyrosine residues of IRS (insulin receptor substrate), the intracellular substrates thereof, and signal transduction is proceeded through recognition and binding of the tyrosine-phosphorylated insulin receptors by Ash/Grb2 or PI-3 kinase, finally resulting in manifestation of biological activities of insulin, such as glucose uptake, sugar metabolism and cell proliferation (see, FIG. 9, Goldstein, B. J. et al., *Receptor*, 3, 1-15, 1993; and Kanai, F. et al. *Biochemical and Biophysical Research Communications*, 195(2), 762-768, 1993). In this signal transduction pathway, however, an enzyme tyrosine phosphatase, which inactivates the activated insulin receptors, i.e., protein tyrosine phosphatase (hereinafter referred to as PTP), has not been progressively studied.

The serious studies of PTPs were initiated after completion of cloning of PTP1B gene and elucidation of the nucleotide sequence thereof by Fischer et al. in 1988, which is cytoplasmic PTP derived from human placenta (Tonks, N. K. et al., *J. Biol. Chem.*, 263, 6722-6730, 1988; Charbonneau, H. et al., *Proc. Natl. Acad. Sci. USA*, 85, 7182-7186, 1988). Consequently, homology to PTP1B could be observed not with the known serine/threonine phosphatases but with two cytoplasmic regions of CD45, a transmembranous molecule involved in a hemopoietic system. Moreover, CD45 was also revealed to have PTP activity (Tonks, N. K. et al., *Biochemistry*, 27, 8695-8701, 1988; and Charbonneau, H. et al., *Proc. Natl. Acad. Sci. USA*, 85, 7182-7186, 1988).

To date, many PTPs have been cloned based on their homologies of cDNA sequences, and new PTPs have been reported subsequently (Streuli, M. et al., *J. Exp. Med.*, 168, 1523-1530, 1988; Krueger, N. X. et al., *EMBO J.*, 9, 3241-3252, 1990; and Trowbridge, I. S. et. al., *Biochim. Biophys. Acta*, 1095, 46-56, 1991). PTPs can be classified generally to: (1) membrane type PTPs having transmembrane region (LCA, leukocyte common antigen, namely CD45, as well as LAR and PTP α, β, γ, δ, ε and ζ), and cytoplasm type PTPs without transmembrane region (PTP1B, TC-PTP, PTP-MEG, PTPH1, STEP and PTP1C).

Many of membrane type PTPs have two PTP homologous domains inside the cell (domain 1 and domain 2, see, FIGS. 1(*a*) and (*b*)). A sequence comprising cysteine (signature motif), Ile/Val-His-Cys-Xaa-Ala-Gly-Xaa-Xaa-Arg-Ser/Thr-Gly (SEQ ID NO: 2), has been conserved in the phosphatase domains between the PTPs reported heretofore. The research on crystallography of PTP1B revealed that the region forms small pockets on the surface of a PTP molecule, and that the cysteine residue is located to the bottom of the pocket, participating directly in binding of the molecule to phosphate (Barford, D. et al., *Science,* 263, 1397-1404, 1994). In addition, it was also revealed that the depth of the pocket of PTP may determine the specificity of serine/threonine phosphatase because phosphate that is binding to serine or threonine cannot reach to the pocket of the enzymatic active center of PTP1B. Moreover, the importance of the above-mentioned signature motif in exhibiting the enzymatic activity has been elucidated (Streuli, M. et al., *EMBO J.,* 9, 2399-2407, 1990). Taking into account of these observations, it has been conceived that the conserved cysteine in domain 1 may play an important role in exhibiting the enzymatic activity, and domain 2 may determine the substrate specificity of the enzyme.

Among a group of PTPs, LAR derived from human is a prototype of receptor type protein tyrosine phosphatases, which was cloned from human placental genome library using a phosphatase domain of CD45, a receptor type protein tyrosine phosphatase, as a probe (Streuli M. et al., *J. Exp. Med.,* 168, 1553-1562, 1988). CD45 is specifically expressed on hemocytic cells, whilst LAR is expressed on the cells other than hemocytic cells, particularly in insulin sensitive organs such as liver and skeletal muscle (Goldstein B. J., *Receptor,* 3, 1-15, 1993). LAR is especially interesting among many types of receptor type PTPs due to its similarity of the extracellular domain with cell adhesion molecules. The entire structure of LAR is elucidated as having 150 kDa of extracellular E-subunit that consists of Ig-like domains and fibronectin type III domains, and 85 kDa of P-subunit comprising a transmembrane region and an intracellular domain having two phosphatase domains, which are covalently bound immediately outside of the cell membrane (see, FIG. 1, Streuli M. et al, *EMBO J.,* 11, 897-907, 1992).

A large number of functional roles of LAR have been reported to date. For example, it was reported that: responses to neurotrophin are decreased in LAR deficient nerves (Yang, T. et al., 27th Annual Meeting of the Society for Neuroscience, New Orleans, La., USA, Oct. 25-30, 1997, Society for Neuroscience Abstracts, 23, 1-2, 1997); secretion of apolipoprotein B is decreased by suppression of LAR activity (Phung, T. L. et al., *Biochemical and Biophysical Research Communications,* 237(2), 367-371, 1997); and loss of expression of LAR diminishes the size of cholinergic nerve cells of prosencephalon basement, thus control by the cholinergic nerve cells at hippocampal dentate gyrus is deteriorated (Yeo, T. T. et al., *J. Neurosci. Res.,* 47(3), 348-360, 1997). In such a manner, it has been gradually revealed that LAR is bearing several important roles in a living body. Furthermore at present, the most remarkable researches are directed to the relationships between LAR and insulin receptors (Hashimoto, N. et al., *J. Biol. Chem.,* 267(20), 13811-13814, 1992).

In 1995, a literature was presented which should be noted, reporting that LAR tyrosine phosphatase activity is abnormally increased in adipose tissue of an obese person, with such an increase being suggested as a cause of onset of insulin resistance and a risk factor of cardiovascular diseases (Ahmad, F. et al., *J. Clin. Invest.,* 95(6) 2806-2812, 1995). Several reports followed thereafter illustrating that LAR is closely concerned with insulin receptors (Mooney, R. A. et al., *Biochemical and Biophysical Research Communications,* 235(3), 709-712, 1997; Orr, S. R et al., *Biochemical Society, Transaction,* 25(3), 452S, 1997; Ahmad, F. et al., *J. Clin. Investigation,* 100(2), 449-458, 1997; Ahmad, F. et al., *J. Biol. Chem.,* 272(1), 448-457, 1997; Norris, K. el al., *Febs Letters,* 415(3), 243-248, 1997; and Li, P. M. et al., *Cellular Signaling,* 8(7), 467-473, 1996). Further, on the basis of such information, Ahmad, F. et al. recently reported that PTP1B may be a therapeutic target of disease states involving in insulin resistance (Ahmad, F. el at, *Metabolism, Clinical and Experimental,* 46(10), 1140-1145, 1997). From the researches to date on PTPs such as LAR, CD45 and the like, it has been elucidated that PTPs bear extremely important roles in an intracellular signaling system.

In 1992, Streuli et al. reported that binding between LAR E-subunit and P-subunit may be dissociated due to the noncovalency of their binding, and thus E-subunit is specifically shed from the cell membrane surface (Streuli, M. et al. *EMBO J.,* 11(3), 897-907, 1992). However, because many researchers have focused the studies using polyclonal or monoclonal antibodies elicited against a LAR E-subunit that is an extracellular domain thereof, a P-subunit even solely having phosphatase activities has been ignored. For example, when an anti-LAR antibody is used intending measurement of LAR phosphatase assay, total phosphatase activity could not be measured unless an antibody to P-subunit is employed. In view of such circumstances, the present inventors started to produce antibodies that specifically bind to a LAR P-subunit, particularly to an intracellular domain thereof, without any specificity to CD45.

Known antibodies to protein tyrosine phosphatase include an antibody generated using 196 amino acid residues as an antigen spanning from the transmembrane region of CD45 to a part of phosphatase domain 1 (Transduction Laboratories). However, it is unclear how these antibodies are immunospecific to phosphatase domains of LAR and the other protein tyrosine phosphatases. Therefore, it was also necessary to produce antibodies which are specific to a LAR intracellular domain but not to CD45.

Thyroid tumors include benign adenoma and malignant carcinoma. At present, palpation, ultrasonic diagnosis, fine needle aspiration cytology, and diagnosis on tissue sections are clinically carried out in order to diagnose thyroid tumors. Thyroid tumors can be classified into adenoma, papillary carcinoma, follicular carcinoma, undifferentiated (anaplastic) carcinoma, medullary carcinoma and malignant lymphoma, whilst thyroid carcinoma (papillary and follicular cancers) can be generally classified into differentiated and poorly differentiated types.

On diagnosis of thyroid carcinoma, if abnormalities were found on palpation and ultrasonic diagnosis, cytological examination with fine needle aspiration has been predominantly carried out because of fewer burdens to the patient, and in difficult cases where definite diagnosis is impossible, additional histological diagnosis is carried out in which thyroid tissue is excised. However, such histological diagnosis imposes more burdens to the patient, and there exist possibilities to excise together with normal tissue. In fact, discrimination by cytological examination is often difficult to draw exact diagnosis, thus many cases have been nevertheless entrusted to histological examination. Additionally, fine needle aspiration cytology does not result in definite diagnosis because cell-cell bindings may be destroyed in those specimens compared to the morphologic observation on tissue sections. Furthermore, in almost cases of follicular carcinoma, discrimination between benign and malignant tumors can be difficult even though histological diagnosis is performed as well as cytological examination. Accordingly, it has been strongly desired by clinicians or pathologists to develop new tools that can discriminate benign/malignant tumors in fine needle aspiration cytology even in such difficult cases for diagnosis as in follicular carcinoma.

SUMMARY OF THE INVENTION

One aspect of the present invention is to provide an antibody that specifically binds to a phosphatase subunit of LAR, particularly an antibody that specifically binds to an intracellular domain of LAR. Further, in accordance with the present invention, an antibody is provided that specifically binds to an intracellular domain of a LAR phosphatase subunit, without specificity to other protein phosphatases.

The antibody may be preferably generated using a polypeptide corresponding to an intracellular domain of LAR, encoded by a nucleotide sequence set forth in SEQ ID NO: 1 or any of fragments thereof as an antigen. Further, preferred antibody may be a monoclonal antibody because of its immunospecific property.

Such an antibody may be generated using a fusion protein comprising a LAR phosphatase domain and another protein or a polypeptide fragment, as an antigen. As the another protein or a polypeptide fragment to be a member of the fusion protein, GST (glutathione-S-transferase) may be particularly suitable, besides, polyhistidine (preferably 6 histidine residues), calmodulin binding peptide (CBP), protein A may be employed.

When polyhistidine is employed, absorption to nickel-chelating resin can be utilized for isolation and purification of the fusion protein expressed by a gene recombinant process, wherein addition of EDTA or imidazole substance as well as pH change may be adopted for dissociating the protein from the resin. When CBP is employed, the expressed fusion protein may be subjected to an affinity chromatography using calmodulin affinity resin, and then may be dissociated from the resin by adding EGTA. In addition, when protein A is employed, the expressed fusion protein may be subjected to an affinity chromatography using IgG sepharose (e.g., IgG Sepharose 6FF), and then may be dissociated from the resin by changing pH.

Moreover, another candidate for a protein or a polypeptide fragment to be employed in the fusion protein may include for example, Xpress, Thioredoxin, c-myc, V5, HA/c-myc and the like. For isolation and purification of the intended fusion protein with a LAR phosphatase domain, expression of the protein may be followed by subjecting to an antigen-antibody affinity column.

The aforementioned preferable immunogen of the present invention, namely a fusion protein of GST and a LAR phosphatase domain, may be suitably produced by: culturing *Escherichia coli* transformed or transfected with an expression vector comprising a coding region of GST gene and a coding region of a phosphatase domain of LAR gene at 20-30° C. for 16-24 hours, preferably at 23-25° C. for 18 hours; and then isolating the fusion protein from the culture fluid and/or bacterial cells. Thus obtained fusion protein may be further purified based on an affinity to a support carrying glutathione, e.g., glutathione sepharose beads, wherein the elution of the fusion protein from the glutathione sepharose beads may be performed by boiling in the presence of a detergent. The detergent may include sodium dodecyl sulfate, CHAPS (3-[(3-cholamide propyl) dimethylammonio]-1-puropane sulfonate), deoxycholic acid, digitonin, n-dodecylmaltoside (1-O-n-dodecyl-β-D-glucopyranosyl (1-4) α-D-glucopyranoside), NONIDET™ P40 (ethylphenolpoly (ethylene glycol ether)n), n-octylglucoside (1-O-n-octyl-β-D-glucopyranoside), sucrose monolaurate, TESIT™ (dodecylpoly (ethylene glycol ether)n), TRITON™ X-100 (octylphenolpoly (ethylene glycol ether)n), TWEEN™ 20 (poly (oxyethylene) n-sorbitan-monolaurate), N-dodecyl-N,N-dimethyl-3-ammonio-1-propanesulfonate, and the like [any of 'n' represents an integer number which is more then or equal to 1]. When elution of the fusion protein is carried out, the resin may be boiled at 100° C. for 5-10 minutes in the presence of such detergents at a concentration that does not lead any problems to an animal to be administered, preferably 0.1% of sodium dodecylsulfate. Accordingly, a purified fusion protein, which is preferable as a contemplated immunogen, can be obtained.

When a monoclonal antibody is generated using such a fusion protein as an immunogen, a LAR phosphatase subunit may be employed for screening the antibody, however, it is more preferable to perform the screening using the fusion protein as an immunogen in terms of the specificity.

The exemplary monoclonal antibody of the present invention may include a monoclonal antibody having a molecular weight of about 150 kDa that is produced from mouse/mouse hybridoma cells. The antibody can be applied as a tool for further elucidation of the mechanisms of an insulin signaling system, for developing useful diagnostic methods of insulin resistance and NIDDM, and for prophylaxis, therapeutics and diagnosis of several kinds of pathological states relating to syndrome X based on insulin resistance. Moreover, the antibody of the present invention may be useful for identification and acquisition of LAR related molecules, for example, modulator, binding protein and the like.

Further aspect of the present invention is to provide a hybridoma cell line producing the above-mentioned monoclonal antibody. Such a hybridoma cell line may include mouse/mouse hybridoma cell line YU1, which was deposited on May 7, 1998, with National Institute of Bioscience and Human-Technology, Agency of Industrial Science and Technology 1-1-320, Rigashi, Tsukuba, Ibaraki, JAPAN, and assigned Accession No. FERM BP-6343.

The antibody of the present invention has specific immunoreactivity with LAR protein, and fragments and polypeptides that comprise at least a LAR intracellular domain (the fragment and polypeptide are hereinafter collectively referred to as 'LAR derived molecules'), which was derived from natural sources, or wholly or partially synthesized (such as those chemically synthesized, or recombinantly synthesized).

Another aspect of the present invention is to provide a method for generating an antibody having specificity to a LAR phosphatase subunit, wherein the aforementioned fusion protein comprising a LAR phosphatase domain and another protein or a polypeptide fragment, preferably a GST-LAR phosphatase domain fusion protein, is employed as an immunogen. In this aspect of the present invention, the available another protein or a polypeptide fragment except GST to be a member of the fusion protein, and purification process of the fusion protein are as set forth above.

Further, a fusion protein comprising GST and a LAR phosphatase domain which is a preferable immunogen may be suitably produced by: culturing *Escherichia coli* transformed or transfected with an expression vector comprising a coding region of GST gene and a coding region of a phosphatase domain of LAR gene at 20-30° C. for 16-24 hours, preferably at 23-25° C. for 18 hours, and then isolating the fusion protein from the culture fluid and/or bacterial cells. Thus obtained fusion protein may also be further purified based on an affinity to a support carrying glutathione, e.g., glutathione sepharose beads wherein the elution of the fusion protein from the glutathione sepharose beads may be performed by boiling in the presence of a detergent, as set forth above, and then, for eluting the fusion protein, the resin may be boiled at 100° C. for 5-10 minutes in the presence of the detergent at a concentration which does not lead any problems to an animal to be administered, preferably 0.1% of sodium dodecylsulfate. Accordingly, the purified fusion protein, which is preferable as a contemplated immunogen, can be obtained.

In a method of generating a monoclonal antibody by using such a fusion protein as an immunogen, a LAR phosphatase subunit may be employed for screening the antibody, however, it is more preferable to perform the screening using the fusion protein as an immunogen in terms of the specificity.

The present invention further provides a method of quantitative determination of LAR and/or LAR derived molecules. The method is characterized by comprising the steps of determining an amount of LAR protein and/or a fragment or a polypeptide that comprises at least a LAR intracellular domain, which is contained in a test sample using an antibody set forth above. In this method, the antibody set forth above is used preferably in any of immunoblotting, immunoprecipitation and ELISA, for determining the amount of LAR or LAR derived molecules.

Still another aspect of the present invention is to provide a method for quantitative determination of LAR and/or LAR derived molecules comprising the step of: isolating LAR and/or LAR derived molecules from a test sample using the antibody set forth above, and measuring an activity of the isolated LAR and/or LAR derived molecules. In this method, in order to isolate the LAR and/or LAR derived molecules, affinity chromatography and/or immunoprecipitation by using a support that was bound with the aforementioned antibody are suitably utilized. Namely, affinity chromatography using a column or batch wise method, and/or immunoprecipitation may be performed wherein the support which was previously bound with the antibody is contacted with a test sample to allow specific interaction between antigen (LAR/LAR derived molecules) and antibody, then after washing the unbound antibody, the bound LAR/LAR derived molecules may be eluted.

In yet another aspect of the present invention a method for producing LAR and/or LAR derived molecules is provided, comprising the step of: isolating LAR and/or LAR derived molecules using the antibody set forth above. Isolation of the targeted molecules in the method for production may be suitably carried out by affinity and/or immunoprecipitation by using a support that was previously bound with the antibody, as in the aforementioned method of quantitative determination of LAR and/or LAR derived molecules.

Further aspect contemplated by the present invention is to provide a method for identifying the presence of LAR and/or LAR derived molecules within tissue comprising the step of performing immunohistological examination using the aforementioned antibody. As the immunohistological examination, for example, in situ immunohistological staining with a labelled antibody may be adopted, thus LAR protein and/or a fragment or a polypeptide that comprises at least a LAR intracellular domain, can be detected.

The present invention is further directed to a specific anti-LAR antibody to thyroid carcinoma cells. The antibodies may be those elicited using a LAR molecule as well as the fragment thereof, e.g., a phosphatase domain, an extracellular domain or the like as an antigen, and may include monoclonal and polyclonal antibodies, peptide antibodies, single chain antibodies, chimeric antibodies, humanized antibodies, CDR-grafted antibodies and the like. Particularly, the aforementioned antibodies to a LAR phosphatase subunit, those having immunoreactivity with thyroid carcinoma cells are provided by the present invention. Herein, "having immunoreactivity with thyroid carcinoma cells" means that almost no immunoreactivity with normal thyroid cells or benign tumor thyroid cells (less than or equal to 10% of the normal cells) is exhibited, whilst higher immunoreactivity to the thyroid carcinoma (more than or equal to 20% of the carcinoma cells) is exhibited.

Accordingly, it makes possible to diagnose thyroid cancer through utilizing such an antibody, thus a method for histological diagnosis of thyroid carcinoma is also contemplated by the present invention. The diagnostic method is characterized by comprising the steps of: taking a thyroid tissue sample (specimen) from a subject suspected as suffering from thyroid cancer, and conducting diagnosis of thyroid cancer through evaluating immunoreactivity between the antibody set forth above and the tissue specimen. In this instance, the thyroid tissue specimens may be any of the specimens such as those taken by fine needle aspiration from a subject, or those prepared by excision and extirpation of a part of the thyroid. The diagnostic method where the specimens taken by fine needle aspiration are employed is more preferable in respect of lower invasiveness to the subject. This is an important advantage provided by the present invention taking into account of the nature of the diagnostic method of thyroid cancer based on the histological observation of the tissue, where highly invasive incision procedure has been obliged to practice. Additionally, also in the immunohistochemical diagnostic method utilizing the tissue section, the present invention is more useful because more prominent reliability can be achieved than in the conventional method.

In the above-described diagnostic method, the specimens taken by fine needle aspiration may be evaluated for their immunoreactivity by common in vitro immunoassays e.g., immunoblotting, immunoprecipitation, ELISA or the like, using the antibody of the present invention. In contrast, when tissue sections are used as specimens, conventional immunohistochemical staining techniques can be utilized to determine the immunoreactivity based on immune responses.

Moreover, the present invention provides a composition for histological diagnosis of thyroid carcinoma comprising the aforementioned antibody. Markedly reliable diagnostic method of thyroid cancer as set forth above can be performed using this composition. The composition may include excipient, carrier, buffer, agent for stabilizing the antibody and the like ad libitum, in addition to the antibody.

Consequently, in accordance with the present invention, specific and high expression of LAR in thyroid carcinoma cell was revealed. Furthermore, it was also verified that monoclonal antibody of the present invention is useful for diagnosis of thyroid cancer as illustrated in Examples. Additionally, the monoclonal antibody of the present invention was proven to be useful for the diagnosis of thyroid carcinoma where tissue sections are employed (see. Example 5, 6), and for the diagnosis where homogenized tissue is employed (see, Example 7). From these results, the person skilled in this art will comprehend that the monoclonal antibodies of the present invention are useful for several kinds of cytological or histological diagnoses or biopsy. Moreover, besides the present monoclonal antibodies, monoclonal antibodies, polyclonal antibodies, and/or peptide antibodies that can recognize a LAR extracellular domain may also be utilized in such processes. Again in such cases, the processes may be nevertheless practiced similarly to those where the present monoclonal antibodies are employed, however, effects resulting from release of the extracellular domain would be preferably considered.

It was revealed by the present invention that the antibodies to LAR can be utilized for diagnosis and therapy of diseases related to thyroid carcinoma. An amount of LAR or a fragment thereof may be determined using such an antibody on the basis of immunological binding between them. Specifically, the method of determining an amount of LAR or a fragment thereof may include for example, a sandwich method wherein sandwich complex is detected that was produced by an immunoreaction of LAR or a fragment thereof with an antibody bound to an insoluble support and labelled antibody; and a method wherein an amount of LAR or a fragment thereof in a sample is determined utilizing a competition method by competitively immunoreacting LAR or a fragment thereof and labelled LAR with the antibody, and then determining an amount of LAR or a fragment thereof from the amount of the labelled antigen that bound to the antibody.

When an amount of LAR or a fragment thereof is determined by the sandwich method, a two steps method wherein an immunoreaction of an immobilized antibody with LAR or a fragment thereof is allowed first, then unreacted substances are completely removed by washing, a labelled antibody is added thereto thus a labelled antibody-LAR or a fragment thereof complex is formed; or a one step method wherein an immobilized antibody, a labelled antibody, and LAR or a fragment thereof are simultaneously mixed.

Insoluble support used for such determination may include for example, synthetic resin such as polystyrene, polyethylene, polypropylene, polychlorinated vinyl, polyester, polyacrylate ester, nylon, polyacetal, fluorine contained resin and the like, polysaccharides such as cellulose, agarose and the like, glass; and metal etc. The insoluble support may be in several forms for example, tray-like, spherical, fibrous, cylindrical, discal, vessel-like, cell-like, tubular and so on. The support with the absorbed antibody is stored in a cold place, in the presence of an antiseptic agent such as sodium azide.

For immobilization of an antibody, a known chemical binding method or a physical absorption method may be adopted. The chemical binding method may include for example, glutaraldehyde-utilizing method, maleimide method wherein N-succinimidyl-4-(N-maleimidemethyl) cyclohexane-1-carboxylate, N-succinimidyl-2-maleimideacetate or the like may be used, carbodiimide method wherein 1-ethyl-3-(3-dimethylaminopropyl) carbodiimide hydrochloride may be used. In addition, maleimidebenzoyl-N-hydroxysuccinimide ester method, N-succinimidyl-3-(2-pyridylthio) propionic acid method, bisdiazotized benzidine method, dipalmityllysine method may be included. Alternatively, a complex which was previously formed by a reaction of a detection test material with an antibody of which epitope is in a different kind, may also be captured after the third antibody to said antibody is immobilized according to the method as mentioned above.

The material to be used for labelling the antibody may be enzyme, fluorescent material, luminescence material, radioactive material, metal chelate or the like. An enzyme may include for example, peroxidase, alkaline phosphatase, β-D-galactosidase, malate dehydrogenase, *staphylococcus nuclease*, delta-S-steroid isomerase, α-glycerolphosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholine esterase, and the like; and fluorescent material may include for example, fluorescein isothiocyanate, phycobilin protein, rhodamine, phycoerythrin, phycocyanin, orthophthalic aldehyde and the like; luminescence material may include isoluminol, lucigenin, luminol, aromatic acridiniumester, imidazole, acridinium salt and modified ester thereof, luciferin, luciferase, aequorin and the like; and radioactive material may include $^{125}I$, $^{127}I$, $^{131}I$, $^{14}C$, $^{32}P$, $^{35}S$ and the like, but not limited thereto as long as the material can be used in immunological determination methods. Further, low molecular weight hapten such as biotin, dinitrophenyl, pyridoxal or fluorescamine may be conjugated to the antibody. Preferably horseradish peroxidase may be used as a labelling enzyme. This enzyme can react with a lot of substrates, while being readily conjugated to the antibody by a periodic acid method.

When an enzyme is used as a labelling material, a substrate for measuring its activity, and a color-developing agent are employed. When peroxidase is used as an enzyme, $H_2O_2$ may be used as a substrate solution, and 2,2'-azino-di-[3-ethylbenzthiazolin sulfonate] ammonium (ABTS), 5-aminosalicylic acid, orthophenylenediamine, 4-aminoantipyrine, 3,3',5,5'-tetramethylbenzidine or the like may be used as a color-developing agent; when alkaline phosphatase is employed as an enzyme, the substrate may be orthophenylphosphate, paranitrophenylphosphate or the like; alternatively, when β-D-galactosidase is used as an enzyme, the substrate may be fluorescein-di-(β-D-galactopyranoside), 4-methyl-umbelliferyl-D-galactopyranoside, or the like.

The present invention further contemplates a kit, which comprises the above-described monoclonal antibody or polyclonal antibody, and reagents.

As a crosslinking agent, N,N'-orthophenylenedimaleimide, 4-(N-maleimidemethyl) cyclohexanoyl N-succinimide ester, 6-maleimidehexanoyl N-succinimide ester, 4,4'-dithiopyridine, orthophenylenedimaleimide, 4-(N-maleimidemethyl) cyclohexanoyl N-succinimide ester, 6-maleimidehexanoyl N-succinimide ester, 4,4'-dithiopyridine, or other known crosslinking agents can be utilized. The reaction of such a crosslinking agent with the enzyme and the antibody may be proceeded in accordance with known methods depending upon the properties of the crosslinking agent that was employed.

Additionally, the antibodies to be used may be any fragments of these antibodies for example, Fab', Fab, $F(ab')_2$ depending on conditions. Furthermore, an enzymatically labelled antibody can be obtained by a similar process in either case of polyclonal antibody or monoclonal antibody, whichever. When the enzymatically labelled antibody that was obtained by using the aforementioned crosslinking agent is purified by any known methods, more sensitive immunological determination system can be achieved. The enzymatically labelled antibody that was purified in such a manner may be mixed with a stabilizer such as thimerosal, glycerol or the like, alternatively, may be lyophilized, and then stored in a cold and dark place.

The present invention further provides a DDS (Drug Delivery System) formulation that was targeted to thyroid carcinoma cells using the above-described antibody having specific immunoreactivity to thyroid carcinoma cells.

It have been elucidated that several genes are involved in thyroid carcinoma. Mutations in tyrosine kinase domain of Ret or TRK gene were found in some of the patients suffering from papillary carcinoma (Fusco, A. et al., *Nature*, 328, 170-2, 1987). Moreover, mutation in Ret gene was observed in 3-30% of the papillary carcinoma patients without any history of a radiation exposure in the past (Santoro, M. et al, *J. Clin. Invest.*, 89, 1517-22, 1992; Bongdrzone, I. et al. *J. Clin. Endocrinol. Metab.*, 81, 2006-9, 1996; Zou, M. et al., *Cancer*, 73, 176-80, 1994), whilst higher incidence of 60-80% of the Ret mutation was observed in papillary carcinoma diagnosed, for children with experiences of radiation exposure on the disaster at Chernobyl nuclear power plant, or the patients who have case histories of radiation exposure in their childhood (Fugazzola, L. el at, *Cancer Res.*, 55, 5617-20, 1995; Klugbauer, S. el a., *Oncogene*, 11, 2459-67, 1995; Nikiforov, Y. E. et al., *Cancer Res.*, 57, 1690-4, 1997; Bounacer, A. et al. *Oncogene*, 15, 1263-73, 1997), and frequency of TRK gene mutation is significantly low (Bongdrzone, I. et al., *J. Clin. Endocrinol. Metab.*, 81, 2006-9, 1996). Point mutation of Ras gene is frequently observed in goiter and thyroid follicular carcinoma. The basis of this fact is conceived as Ras gene point mutation in an early stage of tumor development (Fagin, J. A., *Molecular pathogenesis.* In: Braverman L E, Utiger R D, eds. Wemer and Ingbar's, the thyroid: a fundamental and clinical text. 7th ed. Philadelphia: Lippincott-Raven, 909-16, 1996; Challeton, C. et al., *Oncogene*, 11, 601-3, 1995). The mutation of genes encoding TSH and stimulatory G protein is reported in some cases of thyroid follicular carcinoma (Challeton, C. el at, *Oncogene* 11, 601-3, 1995; Russo, D. et al. *Oncogene*, 11, 1907-11, 1995). Further, it was also reported that mutation of tumor suppressor gene p53 is rare in differentiated thyroid carcinoma, however, it is frequently found in undifferentiated carcinoma (Fagin, J. A. et al., *J. Clin. Invest.*, 91, 179-84, 1993; Ito, T. et al., *Cancer Res.*, 52, 1369-71, 1992).

According to such known information, a nucleic with the object of therapy or diagnosis of thyroid cancer can be included in a DDS formulation targeted by an antibody to LAR.

Furthermore, it is also known that proliferation of thyroid carcinoma is regulated by thyroid stimulating hormone (TSH), and that suppression of TSH secretion by administrating a thyroid hormone drug may improve recurrence, survival rate or the like of thyroid tumor. Accordingly, a protein, a nucleic acid or a compound that may inhibit TSH stimulation can be also included in the DDS formulation.

On the other hand, the present DDS formulation, which is characterized by targeting to thyroid carcinoma cells using the aforementioned antibody having specific immunoreactivity with thyroid carcinoma cells, may comprise one or more materials which are selected from a group consisting of a nucleic acid, iodine, radioactive iodine, technetium and a protein, accordingly, through including such materials to the formulation, higher targeting ability to thyroid carcinoma is allowed, which can be utilized for therapy or diagnosis of thyroid cancer.

"Nucleic acid" herein refers to for example, a nucleic acid encoding a protein that can be expressed in a host cell, an antisense nucleic acid derived from cells, a nucleic acid of a decoy having a sequence of a gene encoding a binding protein of a cell-derived transcription factor or a sequence of a binding site of a transcription factor, or a similar sequence thereto.

"Antisense nucleic acid" represents a nucleic acid or a nucleic acid sequence that binds specifically to a nucleic acid being able to be expressed in future, at any stage of the gene expression, i.e., replication, transcription, translation or the like, thus inhibits expression of the nucleic acid which can be otherwise expressed in future. Antisense nucleic acid also includes an anti-gene nucleic acid resulting from a triple strand. A nucleic acid encoding a decoy represents a nucleic acid having a sequence of a nucleic acid encoding a binding protein of a cell-derived transcription factor or a sequence of a binding site of a transcription factor, or a similar sequence thereto, thus through introducing the nucleic acid into a cell as a decoy, binding of a transcription factor to its binding site can be inhibited, which may lead to suppression of an action of the transcription factor, finally suppression of a group of genes which was going to be activated may be possibly resulted. "Ribozyme" herein means a nucleic acid that can cut mRNA of a specified protein, then inhibits translation of the specified protein. A ribozyme can be designed from a gene sequence encoding the specified protein, which may include herein irrespective of type of the ribozyme, for example, a hammer head type ribozyme, a hairpin ribozyme, a delta type ribozyme and the like, as long as it can cut mRNA of a specified protein, thus leading to inhibition of translation of the specified protein. Suicide gene herein refers to a gene that leads a cell to death consequently, which may include programmed cell death inducing gene, apoptosis inducing gene, necrosis inducing gene and the like.

These nucleic acids can be selected by a person skilled in this art, and through including these nucleic acids into the DDS formulation, specific death of thyroid carcinoma cells can be achieved.

By adding radioactive iodine ($^{131}$I) to the formulation, normal thyroid cells are destroyed, thus metastasis of carcinoma can be readily detected in systemic radioactive iodine scintillation test. Further, by measuring blood thyroglobulin value, remained carcinoma after operation, or recurrence can be identified. In addition, radioactive iodine therapy makes it possible to prevent from recurrence by destructing latent carcinoma, and systemic radioactive iodine scintillation test can be realized through using of a lot of radioactive iodine for therapy. This test is highly sensitive for finding carcinoma remained. Therefore, by using the antibody of the present invention, or the iodine labelled or radiolabelled antibody, usefulness in diagnosis or therapy may be further improved.

Moreover, the protein may include antibodies, TSH (Thyroid Stimulating Hormone), thyroid hormone and the like.

The above-mentioned DDS formulation comprising the materials as set forth above is useful as a pharmaceutical composition for diagnosis of thyroid cancer, or for pharmaceutical composition for therapy of thyroid cancer.

Furthermore, a pharmaceutical composition of the present invention allows for practicing an effective chemotherapy accompanied by less side effects, through concentrating a drug to the focal portion utilizing an ability of this antibody to bind to thyroid carcinoma cells based on specific immunoreactivity, when a therapeutic treatment of thyroid carcinoma using a chemotherapeutic agent is intended.

Effective chemotherapeutic agent of thyroid carcinoma may include anticancer agent such as cyclophosphamide, adriamycin, streptozotocin, 5-fluorouracil, dacarbazine, vincristine and the like.

An administration process of the above-described pharmaceutical composition may be either of which by systemic administration or topical administration. Systemic administration may include oral administration, intravenous administration, subcutaneous and intramuscular injection, rectal administration, and the like, and topical administration may be preferably performed by direct administration into thyroid tissue, or administration into a vein that is connecting to thyroid tissue.

Dosages of the pharmaceutical composition of the present invention may depend upon the known effective blood concentration level of a drug, which should be determined ad libitum by the skilled person in this art. Additionally, in case of a liposome formulation is prepared, it is important to use the antibody at a dose that does not hamper the liposome formation.

When particularly administered to human, the antibody to be included in the DDS formulation may be preferably the above-described humanized antibody, chimeric antibody or the like without any immunogenicity to human, or with less immunogenicity to the at most. When a mouse monoclonal antibody is administered to a human body, risks of occurrence of various side effects are prospected, because such an antibody is a heterogeneous protein to human. Accordingly, although using a human monoclonal antibody is desirable, fusion efficiencies may be inferior, and obtaining a hybridoma that is stably producing an antibody could be difficult. However, the technologies have been progressing currently, thus generation of human monoclonal antibodies or chimeric antibodies have been enabled.

Chimeric antibody may be a chimeric molecule comprising a mouse antibody and a human antibody. Producing an antibody by immunizing a human with an arbitrary antigen is ethically impossible. Therefore, a mouse is immunized first, then a gene portion of an antibody valuable region (V region) that binds to the antigen of the resulted mouse monoclonal antibody is excised therefrom, and this gene portion is linked to a gene encoding an antibody constant region (C region) from human myeloma, to produce a chimeric gene. When thus prepared chimeric gene is expressed in a host cell, a human-mouse monoclonal antibody can be produced. Because chimeric antibodies are less immunogenic to human, it can be utilized as monoclonal antibodies to be administered to a human body for therapy or diagnostic imaging. Known relevant arts of chimeric antibodies may include Japanese provisional publication No. Hei 05-304989, Japanese provisional publication No. Hei 04-330295, PCT publication No. WO9106649, Japanese provisional publication No. Sho 63-036786, Japanese publication No. Hei 06-98021 and the like.

More recently, however, humanized antibodies were discovered, which are reported to be more useful than chimeric antibodies. Humanized antibody is an antibody of which entire molecule was humanized except for CDR (Complementarity Determining Region) of the antibody molecule, by grafting only CDR encoding gene of the antibody molecule to a gene encoding humanized antibody (CDR). The humanized antibodies have less mouse-derived antibody portion than human-mouse chimeric antibodies, thus they are reported to be less anti-enic and safer. In Japan, clinical tests on humanized antibodies to adult T-cell leukemia have been presently performed. With respect to procedures for producing humanized antibodies and the related arts, see, for example. PCT publication Nos. WO9222653, WO9845332, WO9404679, WO9837200 and 09404679 of Genentech, USA, and PCT publication Nos. WO9429451, WO9429351. WO9413805, WO9306231, WO9201059, WO9116927, WO9116928, WO9109967, WO8901974, WO8901783 of Celltech, United Kingdom and the like.

Method for producing human monoclonal antibodies may include in addition to a cell fusion method, a transformation method with Epstein-Barr virus (EBV), and another fusion method of thus transformed cells and parent cells, a method of producing a chimeric antibody or a humanized antibody utilizing genetic engineering, and the like. A chimeric antibody refers to an antibody prepared by linking immunoglobulin gene fragments of heterologous animals, and a humanized antibody refers to an antibody prepared by modifying a heterologous antibody to human, such as a mouse antibody, wherein a primary structure except for CDR (Complementarity Determining Region) in H chain and L chain is substituted for corresponding primary structure of a human antibody. As parent cells for producing human monoclonal antibody, SHM-D 33 strain (ATCC CRL 1668) or RF-S1 strain may be employed, which is human/mouse heteromyeloma, so that high fusion efficiency that is equal to mouse parent cells can be resulted. Hybridoma obtained using such parent cells can be cloned without feeder cells, and can produce IgG type antibodies in a relatively stable manner, on a large scale. For culturing the parent cells, ERDF medium containing 15% FCS may be employed, and another procedures may be similarly carried out to the case of culture of mouse parent cells. In addition, it is preferable to use sufficiently sensitized human lymphocytes with the antigen, which are colleted from peripheral blood, for producing IgG type human monoclonal antibodies. When obtaining such sufficiently sensitized lymphocytes with an antigen is difficult, in vitro sensitization with the antigen may also be performed.

Using the methods set forth above, the present antibody can be humanized, and thus it is markedly useful for administration to a human body.

In addition, usefulness may be enhanced as a diagnostic/therapeutic drug, through radiolabelling such an antibody with iodine, or including radiolabelled iodine into a pharmaceutical composition that was targeted with the antibody.

When papillary carcinoma or follicular carcinoma invades into surrounding tissue or metastasizes to a distal portion (especially to lung and bone) or lymph node through blood circulation or lymphatically, a common therapeutic strategy for destroying the carcinoma cells has been administration of radiolabelled ($^{131}$-I) iodine. Normal thyroid cells incorporate iodine from the blood and concentrate it. This process is stimulated by TSH (Thyroid Stimulating Hormone) that is secreted from pituitary gland. Iodine is thereafter used to produce thyroid hormone (thyroxine T4). As set forth above, thyroid carcinoma or metastatic area of carcinoma normally incorporates only slight amount of iodine (or radioactive iodine). However, when carcinoma is under influences of abundant TSH, a part of thyroid carcinoma or metastatic one becomes liable to incorporate a significant amount of iodine upon stimulation. Consequently, a large amount of radiation is allowed to be directly exposed to carcinoma without injuring the surrounding tissue. When intact thyroid is present in a body with producing a normal level of thyroid hormone, TSH level that is produced may remain relatively low, however, upon decrease of thyroid hormone level due to removal of whole thyroid or its destruction, pituitary gland rapidly accelerates TSH secretion. The TSH stimulates thyroid carcinoma, leading to incorporation of radioactive iodine. When radioactive iodine therapy is performed for progressed thyroid carcinoma, whole thyroid must be removed almost completely by an operation, and the residual tissue is required to be destroyed using radioactive iodine. Once this procedure is carried out, patients having carcinoma cells remained in the neck area or those having metastatic carcinoma to a distal place are subjected to scanning when their TSH level is high enough, using a test amount of radioactive iodine (normally 2-10 mCi). If substantial amount of radioactive iodine was proved to assemble to a region of thyroid carcinoma, yet more therapeutic amount of radioactive iodine (normally 100-200 mCi: 3700-7400 MBq) is administered in an attempt of destruction of the carcinoma cells. Because radioactive iodine is safe and effective also to the patients having more invasive thyroid carcinoma, many physicians have learned to use radioactive iodine routinely for less invasive papillary carcinoma or follicular carcinoma.

Therefore, by labelling the antibody that binds to LAR using iodine, or by including radioactive iodine into a pharmaceutical composition targeted with the antibody, specificity to thyroid carcinoma cells can be further enhanced, thus therapeutic or diagnostic utilization may be enabled.

Accordingly, an anti-LAR antibody that specifically recognizes thyroid carcinoma cells is also useful in a Drug Delivery System (DDS). Drug Delivery System (Mitsuru Hashida, *Drug Delivery System*, New Challenges to Manufacturing Drugs and Therapy, Kagaku Doujin, (1995)) is a novel technique related to drug administration aiming at: contriving administration routes or forms of drugs; delivering the drugs selectively to targeted sites by controlling pharmacokinetics of the drugs in a body; achieving the optimal therapeutic effects as a result; and minimizing the adverse effects exerted by the drugs. Although various DDS formulations have been developed heretofore, liposome formulations (Hiroshi Terada, Tetsuro Yoshimura eds., Experiment Manual of Liposome in Life Science, Springer-Verlag, Tokyo, (1992)) are among all highlighted in supplementation of a deficient enzyme, administration of carcinostatic agent and antibiotics, as well as in gene therapy.

Liposome is a closed small vesicle composed of a lipid bilayer of which basis is phospholipid that constructs a biomembrane, which is known to be safe with a superior function as a drug carrier, because it can capsulate various drugs irrespective of their solubility whether the drugs may be lipid soluble or water soluble, according to their composition comprising a lipid membrane and an aqueous layered part.

In addition, it is well known that a targeting ability can be imparted to a liposome through binding an antibody, peptide or the like on the surface of the liposome (Kazuo Maruyama, Tomoko Takizawa, Motoharu Iwatsuru et al., *Biochimica et Biophisica Acta* 1234, 74 (1995, Jlbao Zhao, Shunsaku Kimura, Yukio Imanishi, *Biochimica et Biophysica Acta* 1283, 37 (1996)). Accordingly, anti-LAR antibodies can be used for the purpose of improving specificity to thyroid carcinoma cells of various liposome formulations. Further, characteristic features of the liposomes are their abilities to produce a variety of carriers (vectors) of which properties are distinct by alteration of a kind of the lipid, or modifying with polyethylene glycol: for example, temperature sensitive liposomes (Sakae Unezaki, Kazuo Maruyama, Motoharu Iwatsuru et al., *Pharmaceutical Research* 11, 1180 (1994)), liposomes with stability in blood (Kazuo Maruyama, Tsutomu Yuda, Motoham Iwatsuru et al., *Biochimica et Biophysica Acta* 1128, 44 (1992)), cationic liposomes as plasmid introducing vector (Xlang Gao, Daniel Jaffurs, Leaf Huang et al, *Biochemical and Biophysical Research Communications* 200, 1201 (1994)), and the like can be prepared.

However, liposomes are usually incorporated into cells by an endocytotic pathway followed by incorporation into early endosomes proximal to the cell membrane. Then, the liposomes are delivered to late endosomes in a deeper part of the cell, and finally transferred to lysosomes. The liposomes that were transferred to lysosomes are degraded by actions of hydrolytic enzymes, and the drugs capsulated in the liposomes are simultaneously metabolized, therefore, there exists a problem that the accessible rate of the drugs that are kept unchanged into the cytoplasm may be extremely low.

Currently, a method for introducing drugs and the like directly into the cytoplasm without any injury against a cell membrane that is a barrier of a cell has been studied. For example, when liposomes gain an ability to fuse with a membrane, drugs introduced thereinto would be able to be delivered directly into the cytosol without transfer via lysosomes. Methods for fusion of the liposome with a cell have been studied heretofore which may include: pH sensitive liposomes (Kenji Kono. Ken-ichi Zenitani, Toru Takabishi, *Biochimica et Biophysica Acta* 1193, 1(1994)), and reconstituted liposomes that are liposomes incorporated with an envelope protein of virus thereinto (Sangeeta Bagai. Debi P. Sarkar, *The Journal of Biological Chemistry* 269, 1966 (1994)).

Recently, a fusiogenic liposome (HVJ-liposome) was reported, which is a liposome with an imparted ability of Sendai virus (Hemagglutinating Virus of Japan) to fuse with a membrane (Yoshio Okada, *Currenttopics in Membranes and Transport* 32, 297 (1988)). Sendai virus (HVJ) is a pioneering virus for genetics in which animal cells were employed, based on observation of an intercellular fusion event (Y. Maeda, J. Kim, Y. Okada et al., *Experimental Cell Research* 108, 108 (1977)). Furthermore, HVJ can also fuse with liposomes (Mahito Nakanishi, Tsuyoshi Uchida, Yoshio Okada et al., *Experimental Cell Research* 159, 399 (1985)), and the fusion body (HVJ-liposome) can in turn fuse with a cell membrane. Namely, HVJ-liposome that was prepared by a direct reaction between a liposome and HVJ is a so-called hybrid vector, carrying a cavity inside which is derived from the liposome, and an outside spike structure identical to that of a viral envelope. HVJ-liposomes can introduce any substances as long as they can be capsulated into liposomes, such as proteins, chemical substances, genes and the like, into cells at high efficiencies that are equivalent to Sendai virus (Tetsuhiko Nakagawa, Hiriyuki Mizuguchi, Tadanori Mayumi, *Drug Delivery System* 11, 411 (1996)). Additionally, an improved type of HVJ-liposome was proposed wherein introducing efficiencies may be enhanced by co-introduction with DNA and a nuclear protein HNIG-1 (Non-histone chromosomal protein, High Mobility Group-1) having a DNA binding ability (Yasufumi Kaneda et al., *J. Molec. Medicine* 73, 289 (1995)).

Another example of a membrane-fused liposome that can be used is a liposome formulation in which VSV (Vesicular Stomatitis Virus, Yoshiyuki Nagai, Akira Ishihama ed, Protocols for Experiments of Virus, Medical View (1995)) is utilized (*J. Virol.*, 72(7), 6159-63, 1998. *Exp. Cell. Res.*, 200(2). 333-8, 1992, *Proc. Natl. Acad. Sci. USA,* 87(7). 2448-51, 1990; and *Biochim. Biophys. Acta*, 987(1), 15-20, (1989)). VSV is a single strand RNA (−) virus belonging to genus *Vesiculovirus* in family Rhabdovirus, having G protein that is an envelope protein on a membrane surface (Akihiko Kawai, *Journal of Virology,* 24, 826 (1977)). Infection mechanisms of VSV to cells may proceed via an endocytotic pathway similarly to liposomes. However, to be distinct from liposomes, because VSV has a characteristic to fuse with an endosome membrane, VSV introduces its own gene into cytoplasm without degradation by hydrolytic enzymes contained in lysosome. So far, it has been noted that VSV has an ability to fuse with a membrane, and that any hemolytic action is not exhibited against human erythrocyte by VSV (Carole A. Bailey, Douglas K. Miller, John Lenard, *Virology* 133, 111(1984)). Further, because VSV utilizes ubiquitously existing phosphatidylserine in lots of tissue cells as a receptor, wide variety of hosts may be allowed (Michael J. Clague, Christian Schoch, Robert Blumenthai, *Biochemistry,* 29, 1303 (1990)), and propagation of thus virus quickly proceeds, thus characteristics of VSV may be that the virus can be readily collected at a large amount On the other hand, it is reported that VSV and liposome may result in fusion (Satoshi Yamada, Shunichi Ohnishi, *Biochemistry* 25, 3703 (1986)).

As explained in detail, anti-LAR antibodies can be utilized for the purpose of enhancement of targeting abilities of any kinds of liposome formulations, including membrane-fused liposomes, pH sensitive liposomes, reconstitution liposomes, cationic liposomes and the like, or modified types thereof.

Besides, substantive reports on methods for enhancing targeting abilities using monoclonal antibodies and their usefulness have been found (*Hum. Antibodies*, 9(1), 61-5, 1999; *J. Clin. Pharm. Ther.*, 22(1), 7-19, 1997: *J. Int. Med. Res.* 25(1), 14-23, 1997; *Proc. Natl. Acad. Sci. USA*, 93 (24). 14164-9, 1996, *Hepatology*, 22(5), 1482-7, 1995; *Hepatology*, 22(5), 1527-37, 1995, Proc. Natl. Acad. Sci. USA, 92(15), 6986-90, 1995; *Immunomethods*, 4(3), 259-72, 1994; *J. Drug Target*, 2(4). 323-31, 1994; *Cancer Res.*, 57(10), 1922-8, 1997; *Crit. Rev. Biotechnol.*, 17(2), 149-69, 1997; *Methods Find Exp. Clin. Pharmacol.*, 16(7), 505-12, 1994; Trends Biotechnol., 12(6). 234-9, 1994; and *Bioconjug. Chem.*, 4(1), 94-102, 1993), thus monoclonal antibodies to LAR can be used in therapeutic treatment of thyroid carcinoma according to the above-described literatures or known techniques.

Further in addition, anti-LAR antibodies of the present invention can be utilized with contemplation in targeting to thyroid carcinoma, for gene therapy with viral vectors, or for DDS formulations wherein polyacid-glycolic acid microsphere, lipid microsphere, polyethylene glycol-modified enzyme or the like is used.

In still another embodiment of the present invention, high expression of LAR in thyroid carcinoma cells can bring comprehension that high rate of transcription from a LAR molecule-encoding nucleic acid sequence to mRNA followed by translation is conducted in those cells. Accordingly, persons skilled in this art can readily diagnose carcinoma through measuring an expression level of LAR mRNA by using probes for the mRNA.

Furthermore, the present invention can contribute substantially to molecular biological studies on transcription factors, promoters, enhancers, or the like that may accelerate the transcription of LAR in thyroid carcinoma cells.

BEST EMBODIMENT FOR CARRYING OUT THE INVENTION

EXPERIMENTAL EXAMPLE 1

Tyrosine Phosphorylation of Insulin Receptors by LAR Mutants and Studies on Association between LAR and Insulin Receptors First, in order to elucidate signal transduction controlling mechanisms of insulin by LAR, analysis was performed with a strategy in which mutated LAR is used that was prepared by substitution of cysteine with serine, which exists in a catalytic center of PTP domain of LAR.

A) Expression Vector of LAR and Insulin Receptors

Figure 1:
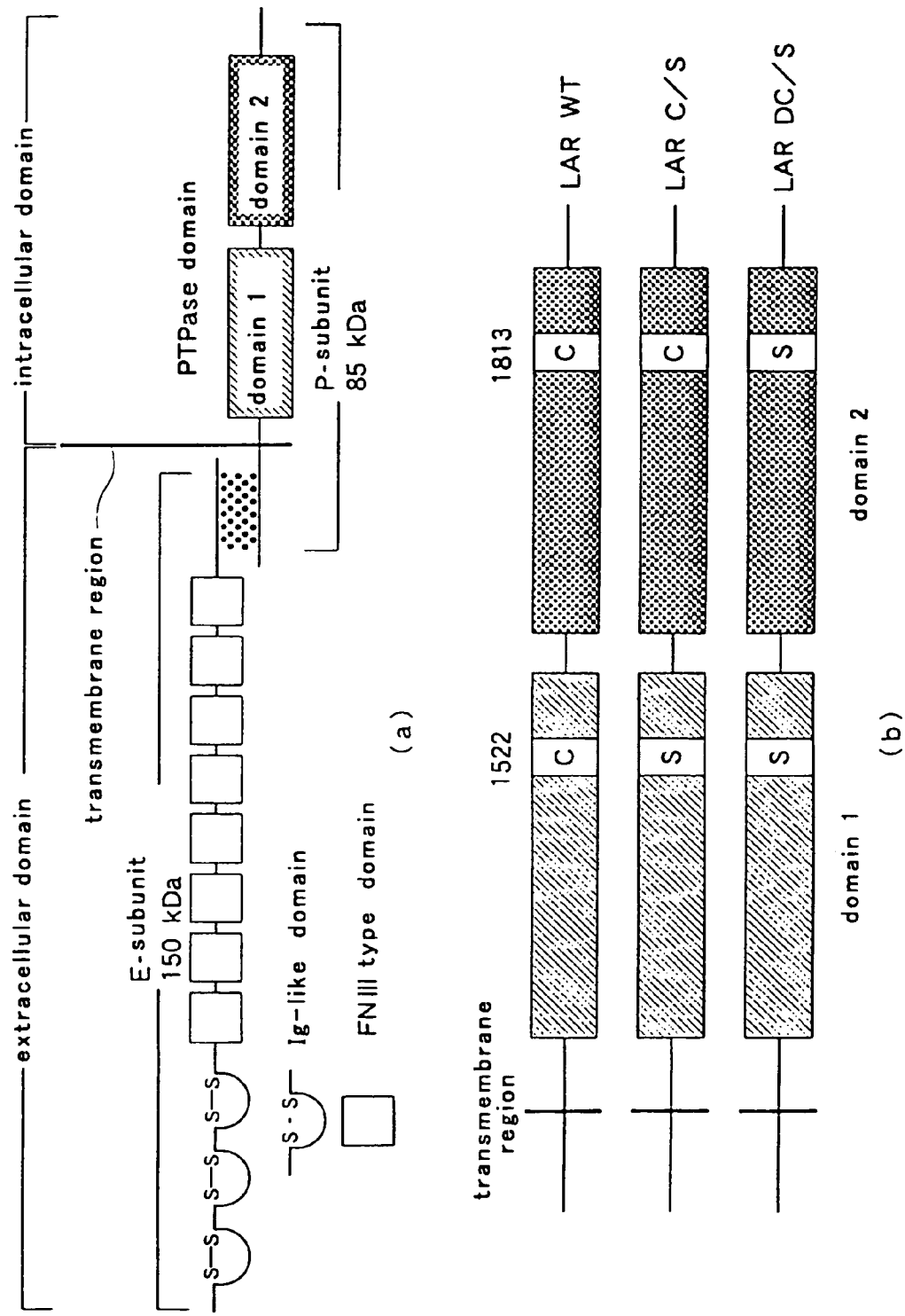
FIG. 1 is a schematic drawing depicting a subunit structure of LAR (a); and a schematic drawing illustrating the mutated LAR phosphatase domain structures inside the membrane (b) prepared as demonstrated in Examples.

Three kinds of LAR expression vectors were used, i.e., (a) LAR WT: human wild type LAR (SEQ ID NO: 3); (b) LAR C/S: mutated LAR, having substitution of cysteine in a catalytic center of LAR-PTP domain 1 (amino acid residue position 1552 of SEQ ID NO: 3) for serine by substituting nucleotide G, position 4983 of SEQ ID NO: 3, with C; and (c) LAR DC/S: further mutated one in addition to LAR C/S, with substitution of cysteine in LAR-PTP domain 2 (amino acid residue position 1813 of SEQ ID NO: 3) for serine by substituting nucleotide G with C, position 5856 of SEQ ID NO: 3 (see, FIG. 1(*b*)), each of which was incorporated into pMT expression vector (see, Streuli M. et al, *EMBO J.,* 11, 897-907, 1992; and Streuli M. et al., *EMBO J,* 9, 2399-2407, 1990).

Meanwhile, insulin receptor expression vectors used were: (a) IR WT: wild type; and (b) IR K1018M: mutated insulin receptor having substitution of lysine of the position 1018 of ATP binding site of wild type insulin receptor, with methionine resulting in deficiency of tyrosine kinase activity, each of which cDNA was incorporated downstream of SRα promoter (see, Kanai F. et al., *Biochemical and Biophysical Research Communications,* 195, 762-768, 1993).

B) Transfection into COS-7 Cells

COS-7 cells were seeded into RPMI 1640 medium (Nissui Pharmaceutical Co., LTD.) supplemented with 10% fetal calf serum at $1.0 \times 10^6$ cells/8 mL/90ϕ dish, then after 16 hours incubation, expression vectors of LAR C/S and IR WT were cotransfected into COS-7 cells using DEAE-dextran method. The LAR C/S employed was a vector that was revealed to include complete deficiency in tyrosine phosphatase activities in vitro (Streuli M. et al, *EMBO J.,* 9, 2399-2407, 1990) according to mutation as mentioned above in paragraph A, (b).

Cotransfection was performed according to the following procedure. Initially, 40 μl of 10 mM chloroquine was added to 4 ml of RPMI 1640 medium (10.2 g/L of RPMI 1640

(Nissui Pharmaceutical Co., LTD.) containing 0.3 g of glutamine and 0.1 g of kanamycin, pH 7.4 that was adjusted with 10% $NaHCO_3$).

To 2 ml of this solution, 5 µg of LAR expression vector and 1 µg of IR expression vector were added, on the other hand, 16 µl of 100 mg/ml DEAE-dextran was added to 2 ml of the remaining solution: Then, both solutions were mixed thoroughly with stirring. Thus prepared 3 75 ml of solution of expression vector was plated at $10 \times 10^6$ cells/8 ml/dish, and was added to COS-7 cells that had been precultured for 16 hours at 37° C., in a 5% $CO_2$ incubator. Following 4 hours culture under the similar conditions to the preculture, the cells were treated with 10% DMSO solution for 2 minutes, then washed with PBS (137 mM NaCl, 2.7 mM KCl, 4.3 mM $Na_2HPO_4.12H_2O$, 1.4 mM $KH_2PO_4$), thereafter, 8 ml of RPMI 1640 containing 10% FCS was added thereto, and cultured for 48 hours at 37° C. within an incubator that was adjusted to 5% $CO_2$.

C) Insulin Stimulation and Preparation of Cell Lysate

COS-7 cells after completing transfection were incubated for 16 hours in serum free RPMI 1640 culture medium, followed by stimulation with $10^{-7}$ M insulin (Seikagaku Corporation) for determined periods, i.e, 0, 1, 5, 15 and 30 minutes. Stimulation for 0 minute was conducted by standing on ice without incubating at 37° C., although insulin was added similarly. After each of the time elapsed from the beginning of insulin stimulation, culture fluid was entirely aspirated from the cells, and 5 ml of PBS w/Inh. (PBS containing tyrosine phosphatase inhibitors: 1 mM sodium vanadate, 5 mM sodium fluoride, 5 mM sodium pyrophosphate, 5 mM EDTA-2Na, 137 mM NaCl, 2.7 mM KCl, 4.3 mM $Na_2HPO_4.12H_2O$, 1.4 mM $KH_2PO_4$) was immediately added.

Following washes of the whole cells with PBS w/Inh., the fluid was removed by aspiration, and 1 ml of lysis buffer (1% Nonidet P-40, 150 mM NaCl, 50 mM Tris-HCl (pH 7.4), 5 mM EDTA, 10 mM Iodoacetamide, 10 mM sodium fluoride, 10 mM sodium pyrophosphate, 0.4 mM sodium vanadate, 0.1 mM oxidized phenylarsine, 1 mM benzamidine, 1 mM phenylmethylsulfonyl fluoride) was added to the cells, which were thereafter collected with a cell scraper. The cell suspension was transferred to a 1.5 ml tube, and then incubated at 4° C. for 30 minutes to result in complete lysis of the cells. Supernatant, which was obtained by centrifuge of the fluid at 12,000 rpm, 4° C. for 10 minutes following incubation was employed as a cell lysate in the experiments set forth below.

D) Immunoprecipitation

Immunoprecipitation was performed for the cell lysate obtained as above paragraph C, with an anti-LAR E-subunit antibody (a mixture of 7.5 µg of 11.1 A and 7.5 µg of 75.3 A, see, Streuli M. et al., *EMBO J.*, 11, 897-907, 1992). To 1 ml of the above cell lysis solution, 15 µg of MOPC 21 (mouse IgG1κ: Sigma Corporation) as a mock was added, then the solution was incubated at 4° C. for one hour, added 20 µl of γ-bind (GammaBind Plus Sepharose: Pharmacia Biotech Inc.) thereto, and further incubated for one hour at 4° C. to execute preabsorption. The solution was centrifuged at 4° C., 12,000 rpm for 10 minutes, then 950 µl of the supernatant was transferred to another tube. Next 15 µg of anti-LAR E-subunit antibody was added to the supernatant, then the solution was incubated at 4° C. for one hour, added 20 µl of γ-bind thereto, and further incubated for one hour at 4° C.

After centrifuge at 4° C., 12,000 rpm for 10 minutes, the precipitate was washed with 1 ml of lysis buffer twice, then once with PBS w/Inh., and suspended in 20 µl of SDS sample buffer. The suspension was heated for 5 minutes in a boiling water bath to prepare a sample for electrophoresis.

E) Immunoblotting

The above-mentioned sample was subjected to electrophoresis using 7.5% SDS-polyacrylamide gel, followed by transfer to a nitrocellulose membrane (Schleicher & Schuell) using a transfer device at 400 mA for 4 hours. Then blocking was conducted by incubating the membrane in 3% bovine serum albumin solution for longer than 30 minutes at a room temperature. After washing with sufficient volume of TBS-T (TBS with Tween 20: 10 mM Tris-HCl (pH 7.4), 150 mM NaCl, 0.1% Tween 20) for 10 minutes more than twice, an anti-phosphotyrosine antibody (4G10, UBI) that was 50,000-fold diluted with TBS-T, the anti-LAR E-subunit antibody or an anti-insulin receptor β-chain antibody (UBI) was added thereto, then the mixture was shaken for one hour at a room temperature. After washing with sufficient volume of TBS-T for 5 minutes more than three times, 15 ml of TBS-T solution containing HRP-labelled anti-mouse IgG antibody (horseradish peroxidase-labelled anti-mouse IgG: Santa Cruz Biotechnology, Inc.) 1.5 ml was added thereto, and shaken for one hour at a room temperature. After washing with sufficient volume of TBS-T for 5 minutes more than three times, bands of the protein were detected that can bind to each of the antibodies, by means of chemiluminescence using a kit of luminescence reagents (Wako Pure Chemical Industries, Ltd.).

F) Results

Figure 2:
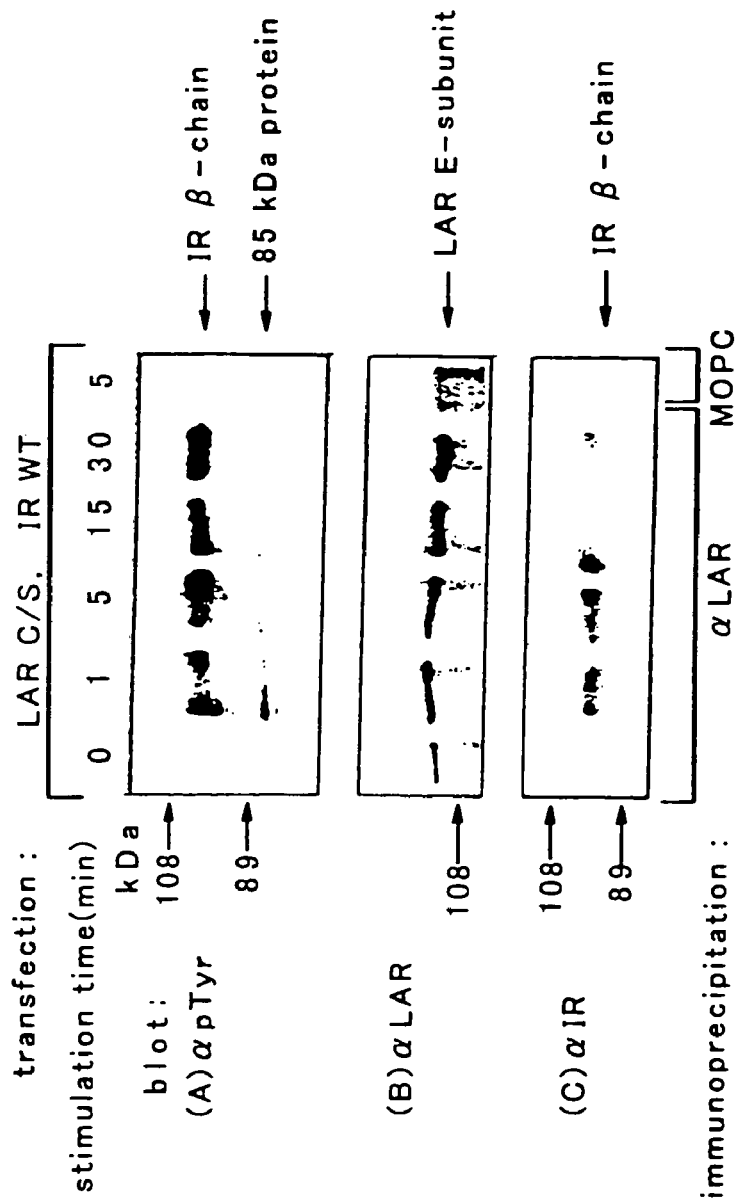
FIG. 2 represents immunoblots illustrating time dependent tyrosine phosphorylation induced by insulin stimulation in COS cells that were cotransfected with LAR/CS and wild type insulin receptor.

As results of immunoblotting with the anti-phosphotyrosine antibody following to immunoprecipitation with the anti-LAR E-subunit antibody of cell lysate prepared after stimulation with insulin for determined time periods of cotransfected COS-7 cells with LAR C/S and IR WT in the above-described manner, tyrosine phosphorylation of an insulin receptor β-chain as well as a 85 kDa protein could be observed with the insulin stimulation for 1 minute. Such tyrosine phosphorylation could also be successively observed with the insulin stimulation for 30 minutes (see. FIG. 2A).

Furthermore, results from the immunoblotting with the anti-LAR E-subunit antibody (FIG. 2B), the anti-insulin receptor β-chain antibody (FIG. 2C) and the anti-phosphotyrosine antibody (FIG. 2A) demonstrated that LAR and insulin receptor may associate depending on the presence or absence of tyrosine phosphorylation of the insulin receptor.

EXPERIMENTAL EXAMPLE 2

Studies on Tyrosine Dephosphorylation of Insulin Receptor by Various LAR (1)

Next, COS-7 cells were similarly cotransfected with LAR WT, LAR C/S or LAR DC/S, and IR VT followed by stimulation with insulin for 5 minutes, immunoprecipitation with the anti-LAR E-subunit antibody, and then immunoblotting with various types of antibodies for the precipitates was carried out. Consequently, tyrosine phosphorylation of the insulin receptor β-chain or the 85 kDa protein could not be detected for the cells cotransfected with insulin receptor and LAR WT, in comparison with the cells cotransfected with LAR C/S or LAR DC/S (see, FIG. 3A).

Additionally in these experiments, amounts of expression of LAR (FIG. 3C) and the insulin receptor (FIG. 3D) were almost identical in both of the cotransfectants, therefore LAR WT was suggested to dephosphorylate the phosphorylated tyrosine of the insulin receptor β-chain as well as the 85 kDa protein (FIG. 3B).

Further, when the immunoprecipitates with the anti-LAR E-subunit antibody were immunoblotted using the anti-insulin receptor β-chain antibody, the cotransfectant with LAR DC/S showed a weaker band of an insulin receptor β-chain, compared to the cotransfectant with LAR WT or LAR C/S.

These results indicate that the association between insulin receptor and LAR DC/S is weaker, when compared with that of LAR WT or LAR C/S. The only one difference between LAR C/S and LAR DC/S is one amino acid residue position 1813 of phosphatase domain 2, accordingly, this domain 2, which was postulated to involve in binding with substrates without tyrosine phosphatase activity, was proved to be playing a role in binding between LAR and insulin receptor.

EXPERIMENTAL EXAMPLE 3

Studies on Tyrosine Dephosphorylation of Insulin Receptor by Various LAR (2)

Figure 4:
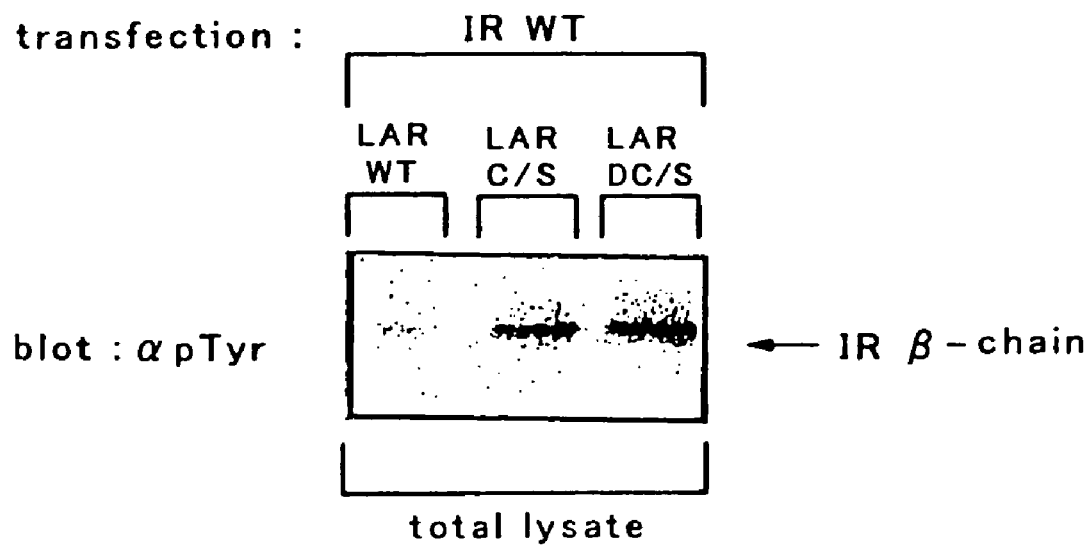
FIG. 4 represents an immunoblot illustrating dephosphorylation of a β-chain of insulin receptor by wild type or mutants of LAR.

In order to further study as to whether tyrosine dephosphorylation of insulin receptor occurs only in cases where LAR was bound, or in every insulin receptor, cell lysate of the cotransfectant was subjected to electrophoresis, and then immunoblotted with the anti-phosphotyrosine antibody. Consequently, tyrosine dephosphorylation of insulin receptor was markedly found only in cells that had been cotransfected with LAR WT (see, FIG. 4).

EXPERIMENTAL EXAMPLE 4

Figure 5:
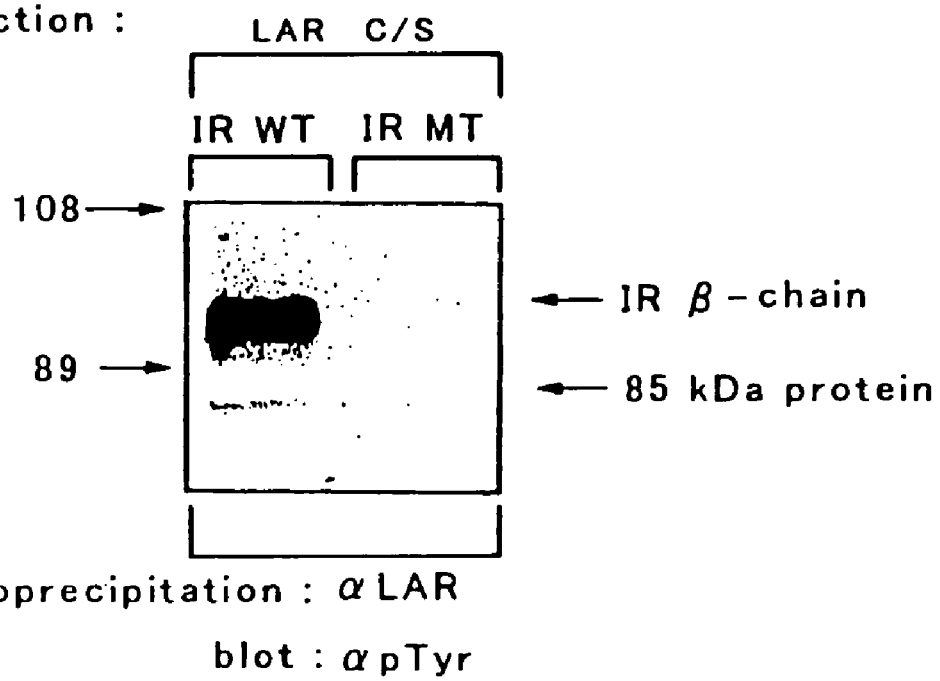
FIG. 5 represents an immunoblot illustrating tyrosine phosphorylation of insulin receptor and LAR in COS cells that were cotransfected with wild type or mutant of insulin receptor, and LAR/CS.

Studies on Tyrosine Phosphorylation of Insulin Receptor in the Presence of LAR C/S In order to elucidate whether tyrosine phosphorylation of the 85 kDa protein is effected by a tyrosine kinase activity of insulin receptor, COS-7 cells were produced that were cotransfected with LAR C/S, and IR WT or IR K 1018 M(IR MT) having a deficiency in tyrosine kinase of insulin receptor. Following insulin stimulation of the cells for 5 minutes, immunoprecipitation was performed with the anti-LAR E-subunit antibody, and immunoblotting with the anti-phosphotyrosine antibody was carried out (see, FIG. 5). Consequently, the cells cotransfected with IR WT showed tyrosine phosphorylation of an insulin receptorβ-chain and the 85 kDa protein upon stimulation with insulin, however, the cells cotransfected with IR K 1018M showed no such phosphorylation at all.

From these results, it was revealed that rapid tyrosine phosphorylation of insulin receptor occurs upon binding of insulin to insulin receptor; and that the insulin receptor tyrosine kinase leads tyrosine phosphorylation of the 85 kDa protein.

The 85 kDa protein was therefore speculated as a P-subunit of LAR of which binding to insulin receptor was demonstrated.

EXAMPLE 1

Generation of Antibodies to an Intracellular Domain of a LAR P-Subunit

Antibodies to an intracellular domain of LAR were generated according to the following procedures.

A) Preparation of Immunogen

Glutathione-S-transferase-LAR fusion protein (GST-LAR) was employed as an immunogen. E. coli AD202 was transformed with an expression vector, pGEX-2T vector (Pharmacia Biotech Inc.), which was incorporated to its BamHI/EcoRI site with cDNA corresponding to 607 amino acids spanning from the end of a transmembrane region of a LAR P-subunit to the entire cytoplasmic region (SEQ ID NO: 1, 3467 bp) according to a general procedure. After the E. coli was incubated overnight in LB (Amp. +) agar medium (LB (Amp. +) described below containing 7.5 g of agar), single colony was inoculated to 50 ml of LB (Amp. +) medium (containing triptone 10 g/L, yeast extract 5 g/L, NaCl 5 g/L, 5 N NaOH 0.2 ml/L, and ampicillin 50 μg/ml), and further incubated overnight. Then the E. coli was inoculated to 500 ml of LB (Amp. +) medium, and incubated at 37° C. until absorbance at 600 nm reaches to approximately 1.0, followed by addition of 50 μl of 1 M IPTG (isopropyl-β-D(−)-thiogalactopyranoside, Wako Pure Chemical Industries, Ltd.) and an incubation at 25° C. overnight. Thus resulted culture was centrifuged at 3,000 rpm, 4° C. for 15 minutes, and the precipitated bacterial bodies were suspended in 50 ml of NETN (0.5% Nonidet P-40, 1 mM EDTA, 20 mM Tris-HCl pH 8.0, 100 mM NaCl). Thereafter, the suspension was subjected to twice repeated treatments of ultrasonication for 1 minute and standing on ice for one minute, and then centrifuged at 14,000 rpm 4° C. for 20 minutes to obtain the supernatant. To 10 ml of the lysate of the E. coli, 100 μl of suspension of glutathione sepharose beads (Glutathione Sepharose 4B (Pharmacia Biotech Inc.) that had been prepared by washing three times, and suspended in 50% NETN) was added, and then incubated for 30 minutes at a room temperature. Thus resulted suspension was centrifuged at 3,000 rpm, 4° C. for 5 minutes, and supernatant was removed. The precipitated glutathione sepharose beads were washed twice with NETN, then once with PBS, thereafter 100 μl of SDS sample buffer (125 mM Tris-HCl pH 6.8, 0.1% sodium dodecylsulfate, 5% 2-mercaptoethanol) was added thereto, and heated in a boiling water bath for 10 minutes to elute the GST-LAR fusion protein. The eluate from which the beads were eliminated was concentrated by centrifuge using Centricon-10 (Amicon) at 3,000 rpm, 4° C. for 45 minutes.

One ml of PBS was added to the concentrate in order to bufferize the solution, and the solution was concentrated again by centrifuge at 3,000 rpm, 4° C. for 45 minutes. This process for bufferization was repeated twice, and thus resulted solution was employed as an immunogen solution. Purification and concentration of the antigenic protein were confirmed by SDS-polyacrylamide gel electrophoresis.

Meanwhile, on a final immunization, the antigen solution was prepared in a different process because it should be administered intravenously. The lysate of the above-described E. coli that is expressing GST-LAR fusion protein was incubated with glutathione sepharose beads, and after centrifuge, the precipitated beads were washed twice with NETN, and three times with PBS. Next, 100 μl of GSH elution buffer (20 mM glutathione, 1M Tris-HCl, pH 9.6) was added thereto, and the mixture was gently stirred for 10 minutes at a room temperature to accomplish the elution of GST-LAR. After repeating the steps of centrifuge at 3,000 rpm, 4° C. for 5 minutes and recovering the supernatant three times, the total eluate was dialyzed in saline at 4° C. for 2 days, then thus obtained solution was employed as an immunogen solution for intravenous administration.

B) Immunization

Eight female Balb/c mice of 6 weeks old received intraperitoneal administration of pristane (2,6,10,14-tetramethylpentadecane, Sigma Corporation) at 0.5 ml/animal. After 2 weeks passed, the antigen solution for intraperitoneal immunization that was emulsified by blending with Freund's complete adjuvant (GDBCO) at a ratio of 1:1 was intraperitoneally administered at about 10 μg of GST-LAR fusion protein per one mouse. Thereafter, the antigen solution for intraperitoneal immunization that was admixed with Freund's incomplete adjuvant (GIBCO) at a ratio of 1:1 was prepared to be about 30-70 μg of GST-LAR per one mouse, and the mixture was intraperitoneally administered approximately once every 2 weeks. On day 4 after the fourth immunization, blood was collected from ocular fundus vein, and an antibody titer in the serum was determined by ELISA method.

C) ELISA

Protein solutions of GST-LAR and GST alone that were prepared similarly to the procedure of preparation of the antigen for intravenous immunization were respectively dialyzed against purified water at 4° C. overnight. These solutions were adjusted to 0.5 μg/ml in PBS, and subjected to absorption to an ELISA plate (Falcon 3911 MicroTest™ Flexible Assay Plate) at 50 μl/well for one hour. After five times washes with wash buffer (PBS containing 0.05% Tween20), blocking with 5% skim milk (prepared by dissolving 2.5 g of skim milk in 50 ml of PBS) was conducted. Following washes, the serum as obtained in the above section B was diluted to 16,000 fold with dilution buffer (PBS containing 0.25% BSA), and was added to the wells at 50 μl/well, and then incubated for one hour in a wet box. After washing the plate, HRP-labelled anti-mouse IgG antibody that was diluted to 1,000 fold was added to the plate at 50 μl/well, and incubated for one hour. Following washes with wash buffer four times and once with PBS, a substrate solution of o-phenylenediamine (Wako Pure Chemical Industries, Ltd.) that was dissolved in a citrate buffer (prepared by dissolving 5.6325 g of citric acid monohydrate and 18.35 g of $Na_2HPO_4.12H_2O$ in purified water to make 500 ml in total) at a concentration of 1 mg/ml was added at 50 μl/well, allowed for reaction for 30 minutes, and then 50 μl of 10% $H_2SO_4$ was added to terminate the reaction. Fifty μl of the solution was transferred to each well of a 96-well plate (Sumitomo Bakelite Co., LTD.) for measurement, and then absorbance at 450 nm was measured.

D) Cell Fusion

Two mice that showed elevation of the antibody titers to GST-LAR in accordance with the results of the above ELISA were finally immunized, and spleen was excised therefrom on the third day to prepare splenocytes according to an ordinary procedure.

Parent cells employed for cell fusion were Balb/c mouse-derived myeloma cell strain NS1 that was previously selected in a medium containing 20 μg/ml 8-azaguanine, and confirmed as hypoxanthine, guanine, phosphoribosyl transferase (HGPRT) deficient strain. Cell fusion, HAT selection and cloning were performed with $2 \times 10^7$ of NS1 cells and $1 \times 10^8$ of splenocytes, using ClonaCell™—HY Hybridoma Cloning Kit (StemCell Technologies Inc.).

Screening of the supernatant from the culture of the cloned hybridoma was carried out according to ELISA method described in section C above, with 50 μl of the supernatant of hybridoma culture using plates bound with 0.5 μg/ml protein solution of GST, GST-LAR or GST-CD45 (Furukawa, T. et al., *Proc. Natl. Acad. Sci. USA*, 91, 10928-10932,1994) prepared by the similar method for preparation of the antigen for intravenous immunization as described above. In this ELISA method, hybridoma was selected, which did not show any immune response to the wells bound with GST or GST-CD45, but showed an immune response only to the wells bound with GST-LAR. Passage culture of the cloned hybridoma was conducted with RPMI 1640 medium (Nissui Pharmaceutical Co., LTD.) containing 10% fetal bovine serum (GIBCO).

Through screening by ELISA method of the culture supernatant in this manner from the hybridoma that was HAT selected, a clone YU1 having specificity to LAR intracellular domain, with stable antibody producibility and proliferation ability could be obtained.

This hybridoma cell line YU1 was deposited on May 7, 1998, with National Institute of Bioscience and Human-Technology, Agency of Industrial Science and Technology, 1-1-320, Higashi, Tsultuba, Ibaraki, JAPAN, and assigned Accession No. FERM BP-6343.

E) Typing of Monoclonal Antibody

Supernatant of 0.5 ml from culture of hybridoma YU1 obtained in the above section D was diluted with 4.5 ml of TBS-T, and isotype was determined for 3 ml of the diluted solution using mouse monoclonal antibody isotyping kit (Amersham International pic.). As a result, the isotype of the antibody was proved to be IgG2bκ.

F) Generation and Purification of Monoclonal Antibody

Balb/c mice of 6 weeks old received intraperitoneal administration of pristane at 0.5 ml/animal, and after 10 days, hybridoma cell YU1 that was obtained by cloning in section D above was intraperitoneally injected at $2.5 \times 10^6$ - $1.3 \times 10^7$ cells/0.5 ml/animal. Abdominal hypertrophy was observed approximately 10 days thereafter, accordingly, ascites fluid was collected using a 20-gauge injection needle several times. Thus collected ascites fluid was centrifuged at 1,000 rpm, 4° C. for 5 minutes to separate supernatant and precipitate. The supernatant was incubated at 37° C. for 30 minutes, and stood at 4° C. overnight. Following centrifuge at 12,000 rpm, 4° C. for 10 minutes, the monoclonal antibody YU1 was purified using an affinity column HiTrap ProteinG (Pharmacia Biotech Inc.) from the resulted 1.5 ml of supernatant. Concentration of the antibody was calculated from molecular extinction coefficient of mouse IgG, based on the measured absorbance at 280 nm of the antibody solution thus obtained.

Figure 6:
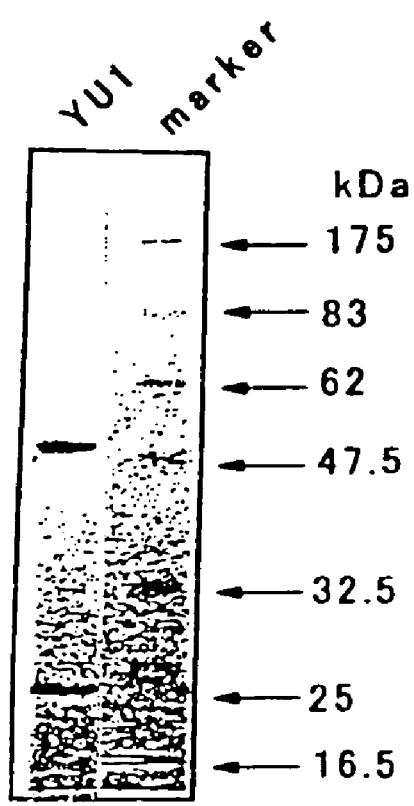
FIG. 6 represents SDS-polyacrylamide gel, showing a molecular weight of the antibody YU1 of the present invention.

In addition, a molecular weight of the monoclonal antibody YU1 was estimated from mobility on SDS-polyacrylamide gel electrophoresis. The results are shown in FIG. 6. As is clear from the FIG. 6, monoclonal antibody YU1 comprises H-chain of about 50 kDa and L-chain of about 25 kDa, haling a total molecular weight of about 150 kDa.

EXAMPLE 2

Studies on Specificity of Monoclonal Antibody

An expression vector of LAR WT was transfected into COS-7 cells according to the procedures described in Example 1, sections A and B. Following immunoprecipitation of the cell lysate with the purified monoclonal antibody obtained in Example 1, immunoblotting was carried out. As a control on immunoprecipitation, MOPC 21 for the antibodies belonging to IgG1 subclass (the anti-LAR E-subunit antibody (supra) and an anti-CD45 antibody (Santa Cruz Biotechnology, Inc., 35-Z6)), or mouse IgG2b κ (MOPC 195, CAPPEL) for the monoclonal antibody YU1 was employed.

Figure 7:
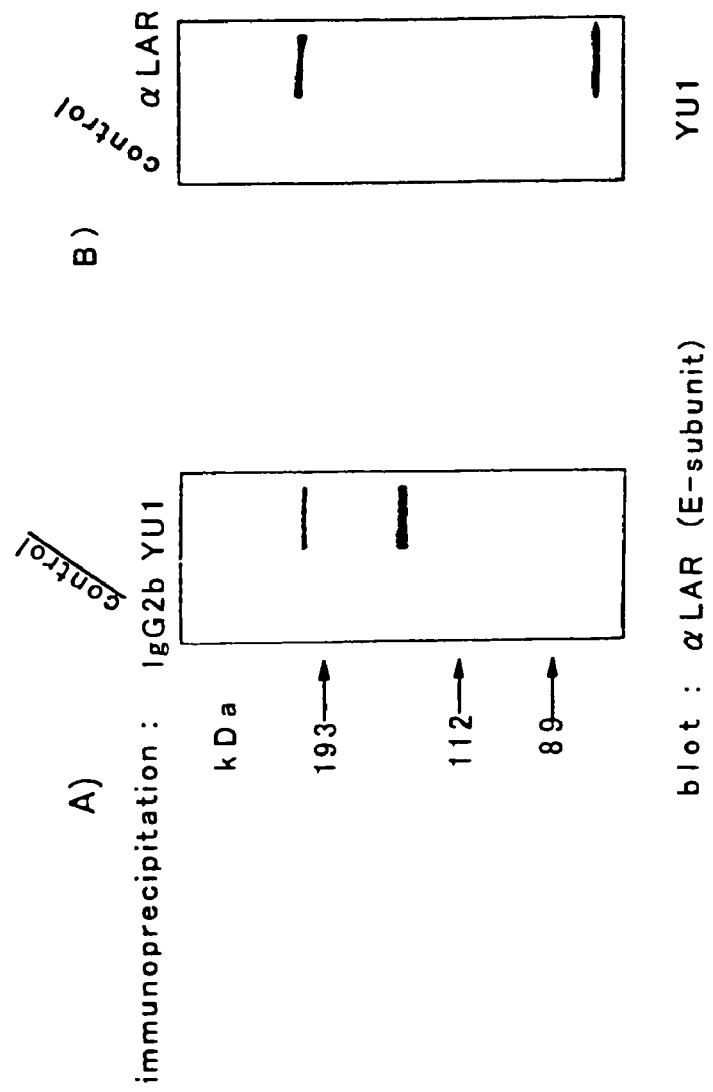
FIG. 7 represents immunoblots showing immunospecificity of the antibody YU1 of the present invention.

From the analyses using the LAR enforced expression system in COS-7 cells, the monoclonal antibody YU1 recognized proteins of 85 kDa that corresponds to a LAR P-subunit and of about 200 kDa that corresponds to a precursor, after immunoprecipitation with the anti-LAR E-subunit antibody (see, FIG. 7B).

Moreover, upon immunoblotting with an antibody that recognizes a LAR E-subunit after immunoprecipitation of cell extract of COS-7 cells transfected with LAR using these antibodies (IgG1, IgG2b, or YU1), detection of proteins of 150 kDa that corresponds to a LAR E-subunit and of about 200 kDa that corresponds to a precursor was restricted only to that immunoprecipitated with the antibody YU1 (see, FIG. 7A). From the results above, it was revealed that the monoclonal antibody YU1 could be utilized for immunoprecipitation and immunoblotting of a LAR P-subunit.

EXAMPLE 3

Phosphorylation of LAR by Insulin Receptor Tyrosine Kinase

Experimental Example 4 suggested a possibility that a tyrosine phosphorylated 85 kDa band that was detected with cotransfection of insulin receptor and LAR may be a P-subunit of LAR.

Accordingly, studies were conducted using the monoclonal antibody YU1, which was generated in Example 1, as to whether the 85 kDa protein of which tyrosine was phosphorylated by insulin receptor tyrosine kinase, was a LAR P-subunit according to a similar procedure described in Example 1.

Cell lysate of COS-7 cells stimulated with insulin for 1 minute following cotransfection of LAR WT or LAR C/S with IR, was immunoprecipitated with the anti-LAR E-subunit antibody, and then immunoblotted with a mixture of the anti-LAR E-subunit antibody and the antibody YU1, thus a precursor of LAR and each subunit were detected.

Figure 8:
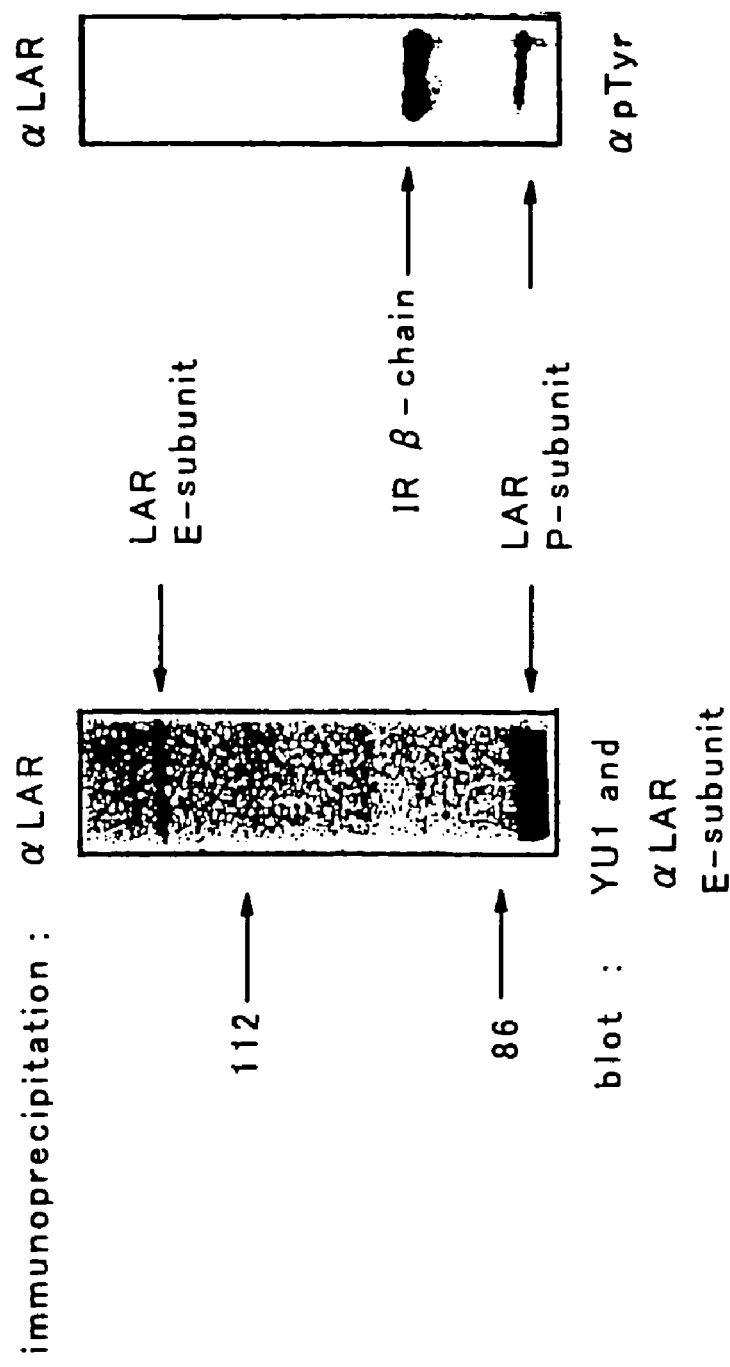
FIG. 8 represents immunoblots showing tyrosine phosphorylation of LAR by tyrosine kinase of insulin receptor.

Further reprobe of this blot with the anti-phosphotyrosine antibody showed agreement of the 85 kDa tyrosine phosphorylated band with a band of a LAR P-subunit (see, FIG. 8). These results illustrate that LAR is one of the substrates of insulin receptor.

Figure 3:
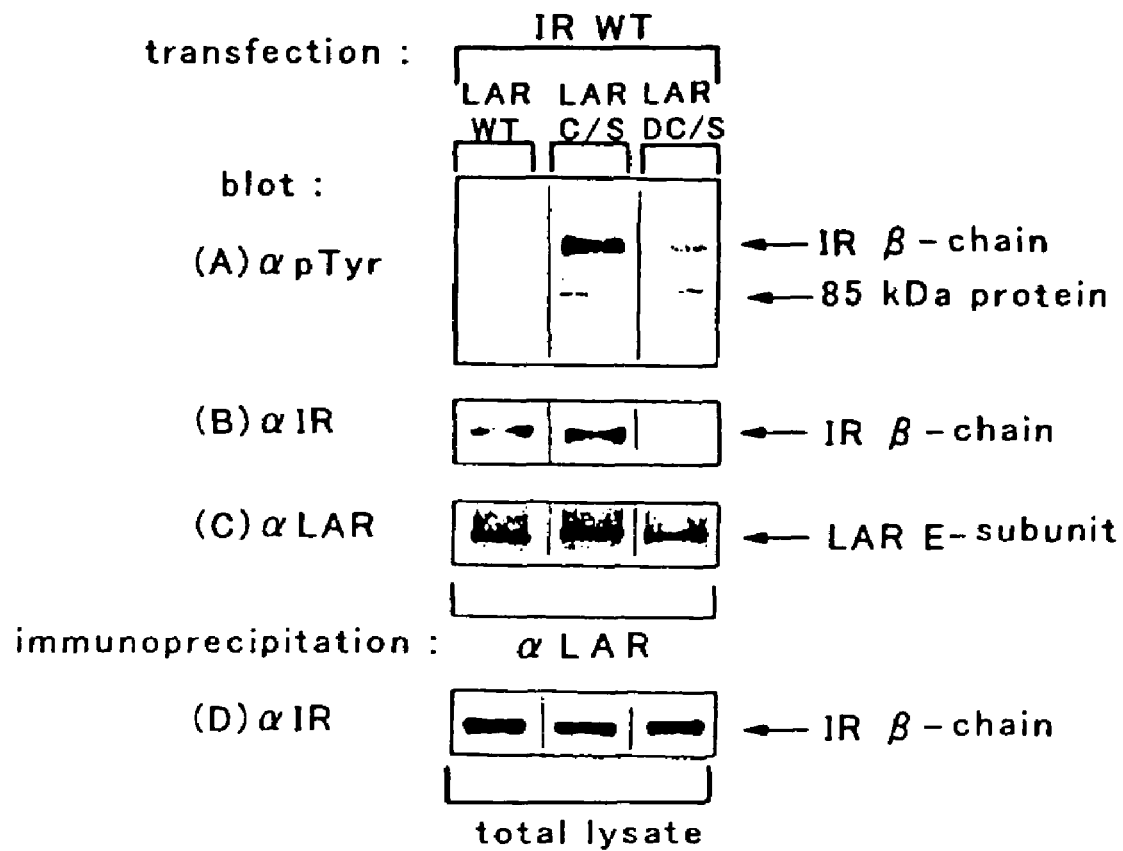
FIG. 3 represents immunoblots illustrating phosphorylation-dephosphorylation in COS cells that were cotransfected with wild type or mutants of LAR, and wild type insulin receptor.

In addition, because the tyrosine phosphorylation of a LAR P-subunit was not detected for the cotransfectant with LAR WT, LAR was supposed to conduct autodephosphorylation (see, FIG. 3).

Figure 9:
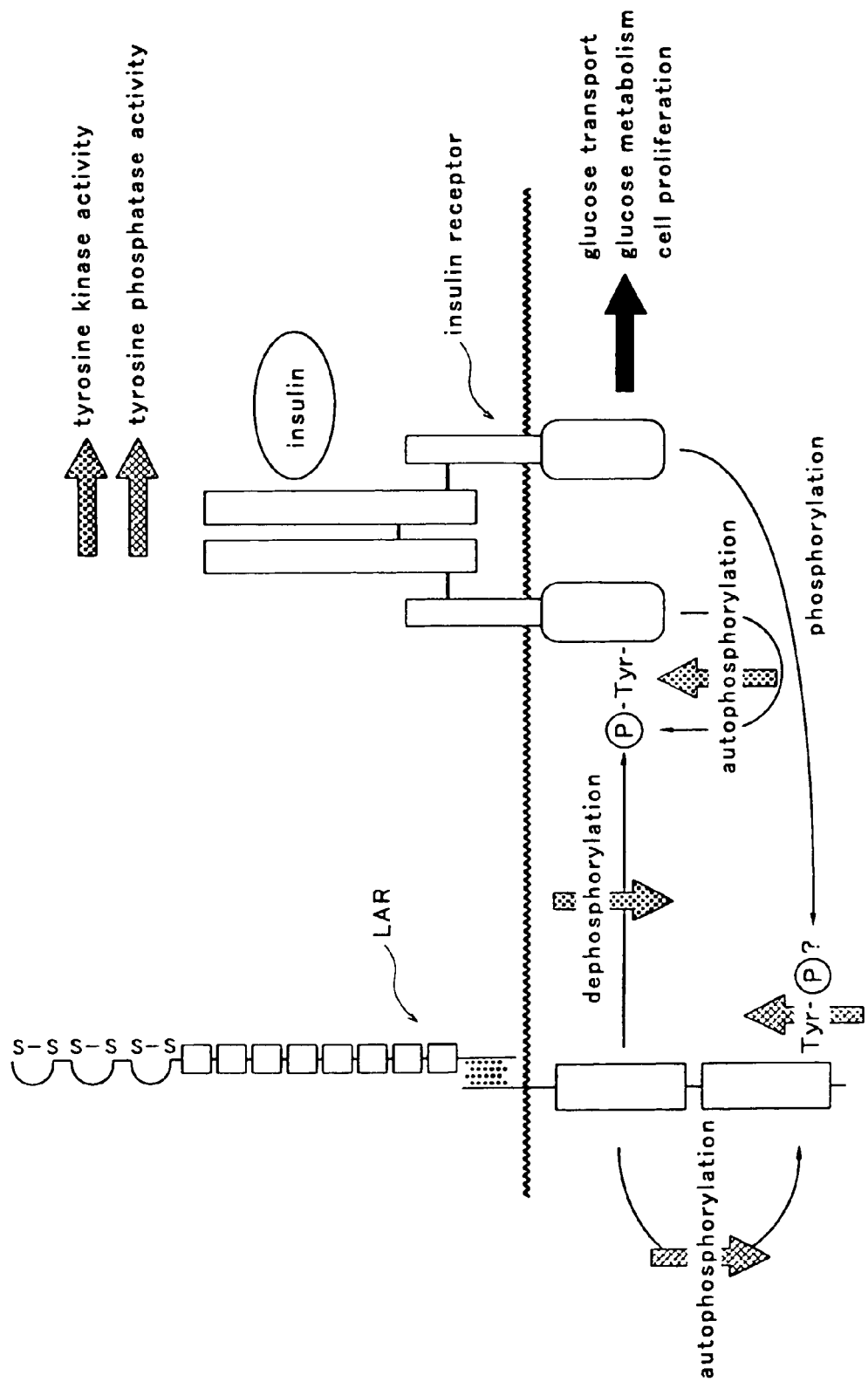
FIG. 9 is a schematic drawing depicting a signal transduction cascade of insulin that is controlled by phosphorylation-dephosphorylation in which insulin receptor and LAR participate.

As shown in FIG. 9, when insulin binds to an insulin receptors α-chain, tyrosine kinase activity is elevated through autophosphorylation of the insulin receptor β-chain. This activity of tyrosine kinase finally results in occurrence of insulin actions such as glucose uptake, glucose metabolism, and cell proliferation. The activated insulin receptor was indicated to be back to an inactive state through tyrosine dephosphorylation by LAR.

Additionally, it was proved that insulin receptor kinase phosphorylates tyrosine of a LAR intracellular domain, and the phosphorylation was speculated to participate in determination of substrate specificity of the LAR intracellular domain or elevation of phosphatase activity. Besides, LAR is conceived as controlling its enzymatic activity through autodephosphorylation of the phosphorylated tyrosine.

From the results set forth above, possibility could be illustrated on a molecular level, that stimulation of enzymatic activity of LAR may be responsible for insulin resistance.

EXAMPLE 4

Tissue Distribution of LAR in Mouse

To one gram of each of the organs that were excised from male C57BL/6 mouse of seven weeks old was added with 3 ml of cold cell lysis buffer (the same buffer as described in Experimental Example 1, section C) followed by homogenization on ice, and incubation for 30 minutes on ice. After centrifuge at 4° C., 15,000×g for 20 minutes, the supernatant was recovered, additionally obtained supernatant by the same centrifuge condition was recovered, then total supernatant was employed as a tissue sample. Protein determination was performed according to a manual of DC Protein Assay (Bio-Rad).

Thus obtained each supernatant (corresponding to 0.2 mg of protein) was electrophoresed, followed by immunoblotting with YU1 according to a procedure described in Experimental Example 1, E.

Figure 14:
FIG. 14 represents results of immunoblotting demonstrating tissue distribution of LAR in mouse using the antibody YU1 of the present invention.

The results of the immunoblotting are shown in FIG. 14. YU1 can also recognize mouse LARK thereby expression in thymus and brain could be identified. Slight expression could be found in kidney and liver as well.

EXAMPLE 5

Immunohistochemical Staining of Thyroid Carcinoma Tissue Section with YU1

Thyroid tissue was fixed in 10% neutral phosphate buffered formaldehyde solution, and embedded in a paraffin block to prepare a specimen on a slide. The detailed procedures are described below.

1) Deparaffination

The fixed paraffin block of the tissue section was immersed in 100% xylene for 5 minutes twice, and then serially immersed in 100% ethanol, 90% ethanol, and 70% ethanol for 3 minutes respectively. Finally, the section was immersed in 10 mM citrate buffer (pH 6.0). In order to make antigen determinants exposed in this state, the specimen was subjected to an autoclave treatment at 100° C., for 5 minutes.

2) Immunostaining

The section was washed with 50 mM Tris-HCl buffer (pH 7.6) containing 0.15M NaCl (Tris solution), and then immersed in this Tris solution. Thereafter, the liquid was wiped away from the slide glass, then the section was dropped with 3% aqueous hydrogen peroxide, and stood for 3 minutes in order to eliminate endogenous peroxidase.

Following sufficient washes with water and additional sufficient washes with Tris solution, the excess liquid was wiped away, and the section was incubated with 50 mM Tris-HCl buffer (pH 7.6) solution containing a carrier protein (2% BSA), 0.015M sodium azide and 0.15M NaCl for 15 minutes to effect blocking.

Next, after the excess liquid was wiped away without washing, primary antibody YU1 (1000 fold dilution of the stock solution) was added on the section, and incubated for 90 minutes in a wet box.

The tissue section was then washed sufficiently with 50 mM Tris-HCl buffer (pH 7.6) containing 0.15M NaCl, and secondary antibody (biotinylated anti-mouse immunoglobulin) was added, followed by incubation for 45 minutes.

Thereafter, the section was sufficiently washed with 50 mM Tris-HCl buffer (pH 7.6) containing 0.15M NaCl, dropped with streptavidin conjugated horseradish peroxidase, and then stood for 25 minutes.

Next, after sufficient washes of the section with 50 mM Tris-HCl buffer (pH 7.6) containing 0.15M NaCl, then 0.05% DAB (3,3'-diaminobenzidine tetra-hydrochloride) solution in 50 mM Tris-HCl buffer (pH 7.6) containing 0.02% hydrogen peroxide and 0.15M NaCl was added, followed by confirmation of color development under microscopy, and then the reaction was terminated by immersion of the slide glass into water.

Following termination of the reaction, the specimen was soaked in Mayer's hematoxylin for 5-10 seconds for counter staining. Thereafter, followed by washes of the specimen with water, and soaking in 100% ethanol for 1 minute twice, next in 100% xylene for 1 minute twice, inclusion with Malinol and observation were carried out.

In these experiments, blocking, secondary antibody, and streptavidin-peroxidase solutions were from LSAB kit available from DAKO Japan Co. Ltd., (Kyoto), and DAB was a commercially available reagent from Dojindo (Kumamoto), Malinol was from Muto Pure Chemicals Ltd., (Tokyo), and Mayer's hematoxylin employed was prepared by the present inventor.

Figure 11:
FIGS. 11-13 represent photos showing positive immunostaining of thyroid carcinoma cells, but not in normal follicular cells using the antibody YU1 of the present invention.
Figure 12:
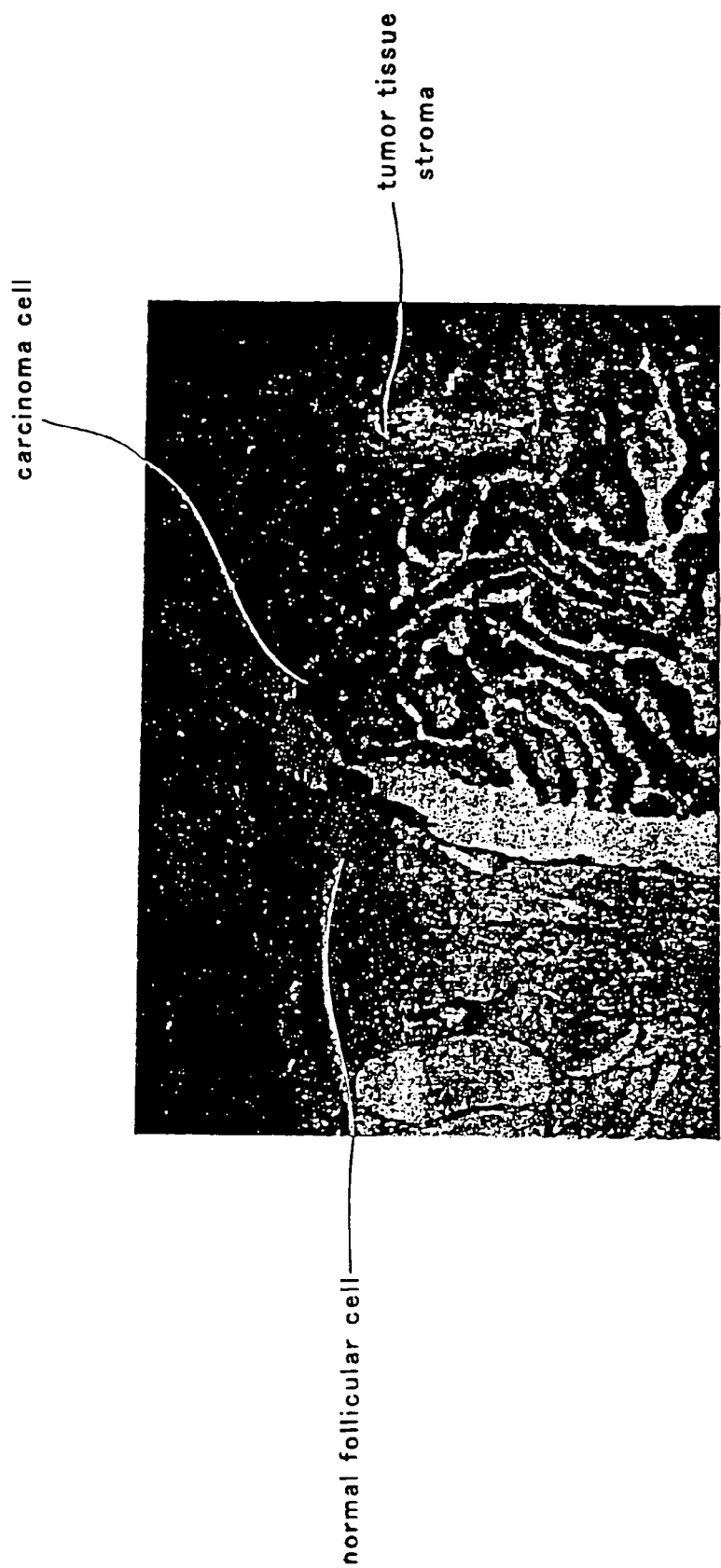
Figure 13:
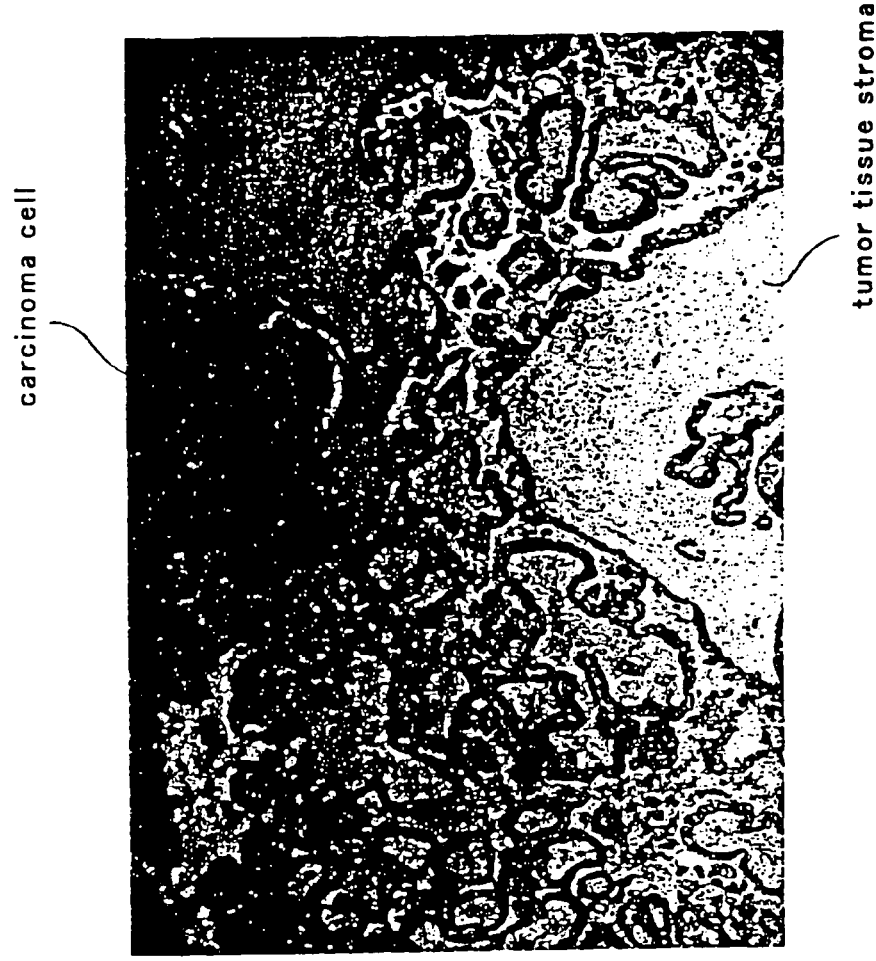

Thus resulted immunohistochemical staining of thyroid papillary carcinoma cells are shown in FIGS. 11-13. These Figures demonstrate selective reactivity of YU1 antibody to thyroid carcinoma cells (brown color stained part), without any reactivity to normal follicular cells and stroma of tumor tissue (blue color stained part).

Accordingly, it was proved that diagnosis of thyroid carcinoma using immunohistochemical staining with the present antibody can be accomplished, and that the present antibody can also be useful in a DDS system comprising anticancer agents (chemotherapeutic agents).

EXAMPLE 6

Immunohistochemical Staining of Another Benign Tumor Cells and Carcinoma Cells

According to the similar procedure in Example 5, immunostaining of various benign tumor and carcinoma cells (that were derived from human) shown in Table 1 below was examined.

Positive results were estimated as appearances of staining based on reactivity to YU1 antibody, and each positivity is presented in Table 1 below.

TABLE 1

|  | Tumor | Number Of Cases | Number of Positive Cases | Positivity |
|---|---|---|---|---|
| Benign | Meningioma | 10 | 0 | 0 |
|  | Thyroid adenoma | 10 | 0 | 0 |
| Malignant | Thyroid carcinoma | 21 | 21 | 100 |
|  | Glioma | 13 | 1 | 7.7 |
|  | Gastric carcinoma | 16 | 1 | 6.3 |
|  | Colon carcinoma | 26 | 13 | 50 |
|  | Lung carcinoma | 20 | 2 | 10 |
|  | Breast carcinoma | 20 | 3 | 15 |
|  | Liver carcinoma | 8 | 0 | 0 |
|  | Kidney carcinoma | 21 | 0 | 0 |
|  | Prostate carcinoma | 32 | 2 | 6.3 |

Consequently, it was obviously shown that the positivity in thyroid carcinoma was 100%, to the contrary, benign tumor and carcinoma originated from another organs showed lower positivity or completely negative. Although comparative higher positivity was shown in colon cancer, normal granular epithelia were also weakly positive, therefore, positive staining presented in colon carcinoma was distinct from that in thyroid carcinoma, accordingly, specific immunoreactivity of YU1 to thyroid carcinoma cells was suggested, with which remarkable staining were observed.

EXAMPLE 7

Specific Immunoreaction of Thyroid Carcinoma with YU1

Studies on Feasibility of Utilizing Immunoassays

To one gram of human thyroid carcinoma and normal tissues that were used in Example 5, 3 ml of cold cell lysis buffer (set forth above in Example 5) was added, and homogenized using Polytron, thereafter, the homogenate was incubated for 30 minutes on ice. Following centrifuge at 4° C., 15,000×g for 20 minutes, the supernatant was recovered, and additionally obtained supernatant by the same centrifuge condition was recovered, then total supernatant was employed as a tissue sample. Protein determination was performed according to a manual of DC Protein Assay (Bio-Rad).

Thus obtained supernatant (corresponding to 1 mg of protein), or immunoprecipitates of COS-7 cells transfected with LAR using the anti-LAR antibody as a positive control (prepared according to the procedures in Example 1A-C) were electrophoresed, followed by immunoblotting with YU1, according to a procedure described in Experimental Example 1, section E. For detection, Immuno Star Reagents (Wako Pure Chemical Industries, Ltd.) was employed.

Figure 10:
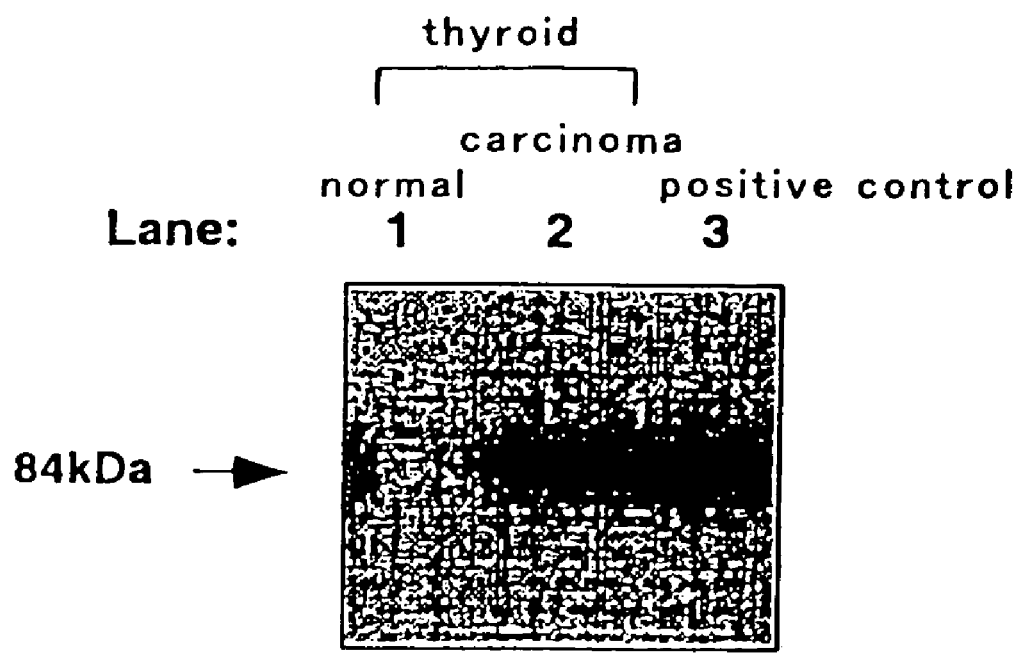
FIG. 10 represents immunoblots of thyroid normal and carcinoma tissues with the antibody YU1 of the present invention, demonstrating the specific immunoreactivity with human thyroid carcinoma tissue.

The results obtained in these experiments are shown in FIG. 10. As is clear from FIG. 10, it was evident that YU1 specifically recognizes the thyroid carcinoma cells, distinct from the normal thyroid cells. Accordingly, it was proved that tissue samples obtained in fine needle aspiration cytology of thyroid could be utilized for diagnosis of thyroid cancer.

INDUSTRIAL APPLICABILITY

The antibodies to a LAR phosphatase subunit that is provided by the present invention can specifically recognize an intracellular domain of LAR having phosphatase activity. Therefore, the antibodies can be extremely useful tools for elucidating signal transduction mechanisms of insulin, and for identifying, obtaining LAR modulators, binding proteins, and the like. Furthermore, the antibodies can be applied for developing useful diagnostic methods of insulin resistance and NIDDM, for prophylaxis and diagnosis of various disease states of syndrome X that is based on insulin resistance, and for prophylaxis and diagnosis of onset of arteriosclerosis and cardiac diseases.

Additionally, because the antibodies of the present invention have specific immunoreactivity to thyroid carcinoma, they are useful in diagnosis of thyroid carcinoma using fine needle aspiration cytology or tissue sections, and in pharmaceutical compositions that utilize DDS for thyroid carcinoma therapy, while they can be helpful to molecular biological studies on transcription of LAR molecules in thyroid carcinoma cells and regulation factors of expression at a translational level.

SEQUENCE LISTING

<160> NUMBER OF SEQ ID NOS: 3

<210> SEQ ID NO 1
<211> LENGTH: 3467
<212> TYPE: DNA
<213> ORGANISM: Homo sapiens
<220> FEATURE:
<221> NAME/KEY: CDS
<222> LOCATION: (6)..(1826)
<220> FEATURE:
<221> NAME/KEY: misc_feature
<222> LOCATION: (213)..(953)
<223> OTHER INFORMATION: Phosphate Domain 1
<220> FEATURE:
<221> NAME/KEY: misc_feature
<222> LOCATION: (1080)..(1826)
<223> OTHER INFORMATION: Phosphatase Domain 2
<300> PUBLICATION INFORMATION:
<308> DATABASE ACCESSION NUMBER: DDBJ/EMBL/GenBank Accession No. Y00815
<309> DATABASE ENTRY DATE: 1995-09-19

<400> SEQUENCE: 1

```
gatcc gga ctg aag gac tcc ttg ctg gcc cac tcc tct gac cct gtg gag      50
      Gly Leu Lys Asp Ser Leu Leu Ala His Ser Ser Asp Pro Val Glu
      1               5                   10                  15 atg cgg agg ctc aac tac cag acc cca ggt atg cga gac cac cca ccc         98
Met Arg Arg Leu Asn Tyr Gln Thr Pro Gly Met Arg Asp His Pro Pro
                20                  25                  30 atc ccc atc acc gac ctg gcg gac aac atc gag cgc ctc aaa gcc aac        146
Ile Pro Ile Thr Asp Leu Ala Asp Asn Ile Glu Arg Leu Lys Ala Asn
            35                  40                  45 gat ggc ctc aag ttc tcc cag gag tat gag tcc atc gac cct gga cag        194
Asp Gly Leu Lys Phe Ser Gln Glu Tyr Glu Ser Ile Asp Pro Gly Gln
        50                  55                  60 cag ttc acg tgg gag aat tca aac ctg gag gtg aac aag ccc aag aac        242
Gln Phe Thr Trp Glu Asn Ser Asn Leu Glu Val Asn Lys Pro Lys Asn
65                  70                  75 cgc tat gcg aat gtc atc gcc tac gac cac tct cga gtc atc ctt acc        290
Arg Tyr Ala Asn Val Ile Ala Tyr Asp His Ser Arg Val Ile Leu Thr
 80                  85                  90                  95 tct atc gat ggc gtc ccc ggg agt gac tac atc aat gcc aac tac atc        338
Ser Ile Asp Gly Val Pro Gly Ser Asp Tyr Ile Asn Ala Asn Tyr Ile
                100                 105                 110 gat ggc tac cgc aag cag aat gcc tac atc gcc acg cag ggc ccc ctg        386
Asp Gly Tyr Arg Lys Gln Asn Ala Tyr Ile Ala Thr Gln Gly Pro Leu
            115                 120                 125 ccc gag acc atg ggc gat ttc tgg aga atg gtg tgg gaa cag cgc acg        434
Pro Glu Thr Met Gly Asp Phe Trp Arg Met Val Trp Glu Gln Arg Thr
        130                 135                 140 gcc act gtg gtc atg atg aca cgg ctg gag gag aag tcc cgg gta aaa        482
Ala Thr Val Val Met Met Thr Arg Leu Glu Glu Lys Ser Arg Val Lys
    145                 150                 155 tgt gat cag tac tgg cca gcc cgt ggc acc gag acc tgt ggc ctt att        530
Cys Asp Gln Tyr Trp Pro Ala Arg Gly Thr Glu Thr Cys Gly Leu Ile
160                 165                 170                 175 cag gtg acc ctg ttg gac aca gtg gag ctg gcc aca tac act gtg cgc        578
Gln Val Thr Leu Leu Asp Thr Val Glu Leu Ala Thr Tyr Thr Val Arg
                180                 185                 190 acc ttc gca ctc cac aag agt ggc tcc agt gag aag cgt gag ctg cgt        626
Thr Phe Ala Leu His Lys Ser Gly Ser Ser Glu Lys Arg Glu Leu Arg
            195                 200                 205 cag ttt cag ttc atg gcc tgg cca gac cat gga gtt cct gag tac cca        674
```

-continued

```
         Gln Phe Gln Phe Met Ala Trp Pro Asp His Gly Val Pro Glu Tyr Pro
                 210                 215                 220 act ccc atc ctg gcc ttc cta cga cgg gtc aag gcc tgc aac ccc cta        722
Thr Pro Ile Leu Ala Phe Leu Arg Arg Val Lys Ala Cys Asn Pro Leu
    225                 230                 235 gac gca ggg ccc atg gtg gtg cac tgc agc gcg ggc gtg ggc cgc acc        770
Asp Ala Gly Pro Met Val Val His Cys Ser Ala Gly Val Gly Arg Thr
240                 245                 250                 255 ggc tgc ttc atc gtg att gat gcc atg ttg gag cgg atg aag cac gag        818
Gly Cys Phe Ile Val Ile Asp Ala Met Leu Glu Arg Met Lys His Glu
                260                 265                 270 aag acg gtg gac atc tat ggc cac gtg acc tgc atg cga tca cag agg        866
Lys Thr Val Asp Ile Tyr Gly His Val Thr Cys Met Arg Ser Gln Arg
            275                 280                 285 aac tac atg gtg cag acg gag gac cag tac gtg ttc atc cat gag gcg        914
Asn Tyr Met Val Gln Thr Glu Asp Gln Tyr Val Phe Ile His Glu Ala
        290                 295                 300 ctg ctg gag gct gcc acg tgc ggc cac aca gag gtg cct gcc cgc aac        962
Leu Leu Glu Ala Ala Thr Cys Gly His Thr Glu Val Pro Ala Arg Asn
305                 310                 315 ctg tat gcc cac atc cag aag ctg ggc caa gtg cct cca ggg gag agt       1010
Leu Tyr Ala His Ile Gln Lys Leu Gly Gln Val Pro Pro Gly Glu Ser
320                 325                 330                 335 gtg acc gcc atg gag ctc gag ttc aag ttg ctg gcc agc tcc aag gcc       1058
Val Thr Ala Met Glu Leu Glu Phe Lys Leu Leu Ala Ser Ser Lys Ala
                340                 345                 350 cac acg tcc cgc ttc atc agc gcc aac ctg ccc tgc aac aag ttc aag       1106
His Thr Ser Arg Phe Ile Ser Ala Asn Leu Pro Cys Asn Lys Phe Lys
            355                 360                 365 aac cgg ctg gtg aac atc atg ccc tac gaa ttg acc cgt gtg tgt ctg       1154
Asn Arg Leu Val Asn Ile Met Pro Tyr Glu Leu Thr Arg Val Cys Leu
        370                 375                 380 cag ccc atc cgt ggt gtg gag ggc tct gac tac atc aat gcc agc ttc       1202
Gln Pro Ile Arg Gly Val Glu Gly Ser Asp Tyr Ile Asn Ala Ser Phe
385                 390                 395 ctg gat ggt tat aga cag cag aag gcc tac ata gct aca cag ggg cct       1250
Leu Asp Gly Tyr Arg Gln Gln Lys Ala Tyr Ile Ala Thr Gln Gly Pro
400                 405                 410                 415 ctg gca gag agc acc gag gac ttc tgg cgc atg cta tgg gag cac aat       1298
Leu Ala Glu Ser Thr Glu Asp Phe Trp Arg Met Leu Trp Glu His Asn
                420                 425                 430 tcc acc atc atc gtc atg ctg acc aag ctt cgg gag atg ggc agg gag       1346
Ser Thr Ile Ile Val Met Leu Thr Lys Leu Arg Glu Met Gly Arg Glu
            435                 440                 445 aaa tgc cac cag tac tgg cca gca gag cgc tct gct cgc tac cag tac       1394
Lys Cys His Gln Tyr Trp Pro Ala Glu Arg Ser Ala Arg Tyr Gln Tyr
        450                 455                 460 ttt gtt gtt gac ccg atg gct gag tac aac atg ccc cag tat atc ctg       1442
Phe Val Val Asp Pro Met Ala Glu Tyr Asn Met Pro Gln Tyr Ile Leu
465                 470                 475 cgt gag ttc aag gtc acg gat gcc cgg gat ggg cag tca agg aca atc       1490
Arg Glu Phe Lys Val Thr Asp Ala Arg Asp Gly Gln Ser Arg Thr Ile
480                 485                 490                 495 cgg cag ttc cag ttc aca gac tgg cca gag cag ggc gtg ccc aag aca       1538
Arg Gln Phe Gln Phe Thr Asp Trp Pro Glu Gln Gly Val Pro Lys Thr
                500                 505                 510 ggc gag gga ttc att gac ttc atc ggg cag gtg cat aag acc aag gag       1586
Gly Glu Gly Phe Ile Asp Phe Ile Gly Gln Val His Lys Thr Lys Glu
            515                 520                 525
```

```
cag ttt gga cag gat ggg cct atc acg gtg cac tgc agt gct ggc gtg      1634
Gln Phe Gly Gln Asp Gly Pro Ile Thr Val His Cys Ser Ala Gly Val
        530                 535                 540 ggc cgc acc ggg gtg ttc atc act ctg agc atc gtc ctg gag cgc atg      1682
Gly Arg Thr Gly Val Phe Ile Thr Leu Ser Ile Val Leu Glu Arg Met
545                 550                 555 cgc tat gag ggc gtg gtc gac atg ttt cag acc gtg aag acc ctg cgt      1730
Arg Tyr Glu Gly Val Val Asp Met Phe Gln Thr Val Lys Thr Leu Arg
560                 565                 570                 575 aca cag cgt cct gcc atg gtg cag aca gag gac cag tat cag ctg tgc      1778
Thr Gln Arg Pro Ala Met Val Gln Thr Glu Asp Gln Tyr Gln Leu Cys
                580                 585                 590 tac cgt gcg gcc ctg gag tac ctc ggc agc ttt gac cac tat gca acg      1826
Tyr Arg Ala Ala Leu Glu Tyr Leu Gly Ser Phe Asp His Tyr Ala Thr
            595                 600                 605 taactaccgc tcccctctcc tccgccaccc ccgccgtggg gctccggagg ggacccagct   1886
cctctgagcc ataccgacca tcgtccagcc ctcctacgca gatgctgtca ctggcagagc   1946
acagcccacg gggatcacag cgtttcagga acgttgccac accaatcaga gagcctagaa   2006
catccctggg caagtggatg gcccagcagg caggcactgt ggcccttctg tccaccagac   2066
ccacctggag cccgcttcaa gctctctgtt gcgctcccgc atttctcatg cttcttctca   2126
tggggtgggg ttggggcaaa gcctccttttt aatacatta agtggggtag actgagggat   2186
tttagcctct tccctctgat ttttcctttc gcgaatccgt atctgcagaa tgggccactg   2246 tagggggttgg ggtttatttt gttttgtttt ttttttttttt ttgtatgact tctgctgaag   2306
gacagaacat tgccttcctc gtgcagagct ggggctgcca gcctgagcgg aggctcggcc   2366
gtgggccggg aggcagtgct gatccggctg ctcctccagc ccttcagacg agatcctgtt   2426
tcagctaaat gcagggaaac tcaatgtttt tttaagtttt gttttcccctt taaagccttt   2486 ttttaggcca cattgacagt ggtgggcggg gagaagatag ggaacactca tccctggtcg   2546
tctatcccag tgtgtgttta acattcacag cccagaacca cagatgtgtc tgggagagcc   2606
tggcaaggca ttcctcatca ccatcgtgtt tgcaaaggtt aaaacaaaaa caaaaaacca   2666
caaaaataaa aaacaaaaaa aacaaaaaac ccaaaaaaaa aaaaaaaaag agtcagccct   2726
tggcttctgc ttcaaacccct caagagggga agcaactccg tgtgcctggg gttcccgagg   2786
gagctgctgg ctgacctggg cccacagagc ctggcttttgg tccccagcat tgcagtatgg   2846
tgtggtgttt gtaggctgtg gggtctggct gtgtggccaa ggtgaatagc acaggttagg   2906
gtgtgtgcca caccccatgc acctcagggc caagcggggg cgtggctggc ctttcaggtc   2966
caggccagtg ggcctggtag cacatgtctg tcctcagagc aggggccaga tgattttcct   3026
ccctggtttg cagctgtttt caaagccccc gataatcgct cttttccact ccaagatgcc   3086
ctcataaacc aatgtggcaa gactactgga cttctatcaa tggtactcta atcagtcctt   3146
attatcccag cttgctgagg ggcagggaga gcgcctcttc ctctgggcag cgctatctag   3206
ataggtaagt gggggcgggg aagggtgcat agctgtttta gctgagggac gtggtgccga   3266 cgtcccccaaa cctagctagg ctaagtcaag atcaacattc cagggttggt aatgttggat   3326
gatgaaacat tcattttttac cttgtggatg ctagtgctgt agagttcact gttgtacaca   3386
gtctgttttc tatttgttaa gaaaaactac agcatcattg cataattctt gatggtaata   3446
aatttgaata atcagatttc t                                              3467
```

<210> SEQ ID NO 2
<211> LENGTH: 11

```
<212> TYPE: PRT
<213> ORGANISM: Unknown
<220> FEATURE:
<223> OTHER INFORMATION: Description of Unknown Organism: Signature
      Motif Conserved in Phosphatase Domain of Known PTPs.
<220> FEATURE:
<221> NAME/KEY: SITE
<222> LOCATION: (1)
<223> OTHER INFORMATION: Xaa= Ile or Val
<220> FEATURE:
<221> NAME/KEY: SITE
<222> LOCATION: (4)
<223> OTHER INFORMATION: Xaa=Unknown
<220> FEATURE:
<221> NAME/KEY: SITE
<222> LOCATION: (7)..(8)
<223> OTHER INFORMATION: Xaa=Unknown
<220> FEATURE:
<221> NAME/KEY: SITE
<222> LOCATION: (10)
<223> OTHER INFORMATION: Xaa= Ser or Thr

<400> SEQUENCE: 2

Xaa His Cys Xaa Ala Gly Xaa Xaa Arg Xaa Gly
 1               5                  10

<210> SEQ ID NO 3
<211> LENGTH: 7702
<212> TYPE: DNA
<213> ORGANISM: Homo sapiens
<220> FEATURE:
<221> NAME/KEY: CDS
<222> LOCATION: (371)..(6061)
<220> FEATURE:
<221> NAME/KEY: sig_peptide
<222> LOCATION: (371)..(418)
<220> FEATURE:
<221> NAME/KEY: mat_peptide
<222> LOCATION: (419)..(6061)
<220> FEATURE:
<221> NAME/KEY: misc_feature
<222> LOCATION: (419)..(4120)
<223> OTHER INFORMATION: Extracellular Domain
<220> FEATURE:
<221> NAME/KEY: misc_feature
<222> LOCATION: (4121)..(4192)
<223> OTHER INFORMATION: Transmembrane Domain
<220> FEATURE:
<221> NAME/KEY: misc_feature
<222> LOCATION: (4193)..(6061)
<223> OTHER INFORMATION: Cytoplasmic Domain
<300> PUBLICATION INFORMATION:
<308> DATABASE ACCESSION NUMBER: DDBJ/EMBL/GenBank Accession No. Y00815
<309> DATABASE ENTRY DATE: 1995-09-19

<400> SEQUENCE: 3
cgggagcggc gggagcggtg gcggcggcag aggcggcggc tccagcttcg gctccggctc      60
gggctcgggc tccggctccg gctccggctc cggctccagc tcgggtggcg gtggcgggag     120
cgggaccagg tggaggcggc ggcggcagag gagtgggagc agcggcccta gcggcttgcg     180
gggggacatg cggaccgacg gcccctggat aggcggaagg agtggaggcc ctggtgcccg     240
gcccttggtg ctgagtatcc agcaagagtg accggggtga agaagcaaag actcggttga     300
ttgtcctggg ctgtggctgg ctgtggagct agagccctgg atggcccctg agccagcccc     360
agggaggacg atg gtg ccc ctt gtg cct gca ctg gtg atg ctt ggt ttg        409
            Met Val Pro Leu Val Pro Ala Leu Val Met Leu Gly Leu
                    -15              -10                  -5 gtg gca ggc gcc cat ggt gac agc aaa cct gtc ttc att aaa gtc cct       457
Val Ala Gly Ala His Gly Asp Ser Lys Pro Val Phe Ile Lys Val Pro
      -1  1               5                  10
```

-continued

| | | |
|---|---|---|
| gag gac cag act ggg ctg tca gga ggg gta gcc tcc ttc gtg tgc caa<br>Glu Asp Gln Thr Gly Leu Ser Gly Gly Val Ala Ser Phe Val Cys Gln<br>15                    20                   25 | 505 |
| gct aca gga gaa ccc aag ccg cgc atc aca tgg atg aag aag ggg aag<br>Ala Thr Gly Glu Pro Lys Pro Arg Ile Thr Trp Met Lys Lys Gly Lys<br>30                    35                   40                   45 | 553 |
| aaa gtc agc tcc cag cgc ttc gag gtc att gag ttt gat gat ggg gca<br>Lys Val Ser Ser Gln Arg Phe Glu Val Ile Glu Phe Asp Asp Gly Ala<br>                50                   55                   60 | 601 |
| ggg tca gtg ctt cgg atc cag cca ttg cgg gtg cag cga gat gaa gcc<br>Gly Ser Val Leu Arg Ile Gln Pro Leu Arg Val Gln Arg Asp Glu Ala<br>            65                   70                   75 | 649 |
| atc tat gag tgt aca gct act aac agc ctg ggt gag atc aac act agt<br>Ile Tyr Glu Cys Thr Ala Thr Asn Ser Leu Gly Glu Ile Asn Thr Ser<br>80                    85                   90 | 697 |
| gcc aag ctc tca gtg ctc gaa gag gaa cag ctg ccc cct ggg ttc cct<br>Ala Lys Leu Ser Val Leu Glu Glu Glu Gln Leu Pro Pro Gly Phe Pro<br>95                    100                 105 | 745 |
| tcc atc gac atg ggg cct cag ctg aag gtg gtg gag aag gca cgc aca<br>Ser Ile Asp Met Gly Pro Gln Leu Lys Val Val Glu Lys Ala Arg Thr<br>110                 115                 120                 125 | 793 |
| gcc acc atg cta tgt gcc gca ggc gga aat cca gac cct gag att tct<br>Ala Thr Met Leu Cys Ala Ala Gly Gly Asn Pro Asp Pro Glu Ile Ser<br>                  130                 135                 140 | 841 |
| tgg ttc aag gac ttc ctt cct gta gac cct gcc acg agc aac ggc cgc<br>Trp Phe Lys Asp Phe Leu Pro Val Asp Pro Ala Thr Ser Asn Gly Arg<br>                  145                 150                 155 | 889 |
| atc aag cag ctg cgt tca ggt gcc ttg cag ata gag agc agt gag gaa<br>Ile Lys Gln Leu Arg Ser Gly Ala Leu Gln Ile Glu Ser Ser Glu Glu<br>160                 165                 170 | 937 |
| tcc gac caa ggc aag tac gag tgt gtg gcg acc aac tcg gca ggc aca<br>Ser Asp Gln Gly Lys Tyr Glu Cys Val Ala Thr Asn Ser Ala Gly Thr<br>175                 180                 185 | 985 |
| cgt tac tca gcc cct gcg aac ctg tat gtg cga gtg cgc cgc gtg gct<br>Arg Tyr Ser Ala Pro Ala Asn Leu Tyr Val Arg Val Arg Arg Val Ala<br>190                 195                 200                 205 | 1033 |
| cct cgt ttc tcc atc cct ccc agc agc cag gag gtg atg cca ggc ggc<br>Pro Arg Phe Ser Ile Pro Pro Ser Ser Gln Glu Val Met Pro Gly Gly<br>                  210                 215                 220 | 1081 |
| agc gtg aac ctg aca tgc gtg gca gtg ggt gca ccc atg ccc tac gtg<br>Ser Val Asn Leu Thr Cys Val Ala Val Gly Ala Pro Met Pro Tyr Val<br>                  225                 230                 235 | 1129 |
| aag tgg atg atg ggg gcc gag gag ctc acc aag gag gat gag atg cca<br>Lys Trp Met Met Gly Ala Glu Glu Leu Thr Lys Glu Asp Glu Met Pro<br>240                 245                 250 | 1177 |
| gtt ggc cgc aac gtc ctg gag ctc agc aat gtc gta cgc tct gcc aac<br>Val Gly Arg Asn Val Leu Glu Leu Ser Asn Val Val Arg Ser Ala Asn<br>255                 260                 265 | 1225 |
| tac acc tgt gtg gcc atc tcc tcg ctg ggc atg atc gag gcc aca gcc<br>Tyr Thr Cys Val Ala Ile Ser Ser Leu Gly Met Ile Glu Ala Thr Ala<br>270                 275                 280                 285 | 1273 |
| cag gtc aca gtg aaa gct ctt cca aag cct ccg att gat ctt gtg gtg<br>Gln Val Thr Val Lys Ala Leu Pro Lys Pro Pro Ile Asp Leu Val Val<br>                  290                 295                 300 | 1321 |
| aca gag aca act gcc acc agt gtc acc ctc acc tgg gac tct ggg aac<br>Thr Glu Thr Thr Ala Thr Ser Val Thr Leu Thr Trp Asp Ser Gly Asn<br>                  305                 310                 315 | 1369 |
| tcg gag cct gta acc tac tat ggc atc cag tac cgc gca gcg ggc acg<br>Ser Glu Pro Val Thr Tyr Tyr Gly Ile Gln Tyr Arg Ala Ala Gly Thr<br>320                 325                 330 | 1417 |

-continued

| | |
|---|---|
| gag ggc ccc ttt cag gag gtg gat ggt gtg gcc acc acc cgc tac agc<br>Glu Gly Pro Phe Gln Glu Val Asp Gly Val Ala Thr Thr Arg Tyr Ser<br>335                            340                        345 | 1465 |
| att ggc ggc ctc agc cct ttc tcg gaa tat gcc ttc cgc gtg ctg gcg<br>Ile Gly Gly Leu Ser Pro Phe Ser Glu Tyr Ala Phe Arg Val Leu Ala<br>350                         355                           360                      365 | 1513 |
| gtg aac agc atc ggg cga ggg ccg ccc agc gag gca gtg cgg gca cgc<br>Val Asn Ser Ile Gly Arg Gly Pro Pro Ser Glu Ala Val Arg Ala Arg<br>                   370                           375                           380 | 1561 |
| acg gga gaa cag gcg ccc tcc agc cca ccg cgc gtg cag gca cgc<br>Thr Gly Glu Gln Ala Pro Ser Ser Pro Pro Arg Arg Val Gln Ala Arg<br>385                            390                        395 | 1609 |
| atg ctg agc gcc agc acc atg ctg gtg cag tgg gag cct ccc gag gag<br>Met Leu Ser Ala Ser Thr Met Leu Val Gln Trp Glu Pro Pro Glu Glu<br>                400                          405                           410 | 1657 |
| ccc aac ggc ctg gtg cgg gga tac cgc gtc tac tat act ccg gac tcc<br>Pro Asn Gly Leu Val Arg Gly Tyr Arg Val Tyr Tyr Thr Pro Asp Ser<br>415                            420                         425 | 1705 |
| cgc cgc ccc ccg aac gcc tgg cac aag cac aac acc gac gcg ggg ctc<br>Arg Arg Pro Pro Asn Ala Trp His Lys His Asn Thr Asp Ala Gly Leu<br>430                            435                           440                      445 | 1753 |
| ctc acg acc gtg ggc agc ctg ctg cct ggc atc acc tac agc ctg cgc<br>Leu Thr Thr Val Gly Ser Leu Leu Pro Gly Ile Thr Tyr Ser Leu Arg<br>                     450                           455                           460 | 1801 |
| gtg ctt gcc ttc acc gcc gtg ggc gat ggc cct ccc agc ccc acc atc<br>Val Leu Ala Phe Thr Ala Val Gly Asp Gly Pro Pro Ser Pro Thr Ile<br>465                            470                        475 | 1849 |
| cag gtc aag acg cag cag gga gtg cct gcc cag ccc gcg gac ttc cag<br>Gln Val Lys Thr Gln Gln Gly Val Pro Ala Gln Pro Ala Asp Phe Gln<br>                480                          485                           490 | 1897 |
| gcc gag gtg gag tcg gac acc agg atc cag ctc tcg tgg ctg ctg ccc<br>Ala Glu Val Glu Ser Asp Thr Arg Ile Gln Leu Ser Trp Leu Leu Pro<br>495                            500                         505 | 1945 |
| cct cag gag cgg atc atc atg tat gaa ctg gtg tac tgg gcg gca gag<br>Pro Gln Glu Arg Ile Ile Met Tyr Glu Leu Val Tyr Trp Ala Ala Glu<br>510                            515                        520                      525 | 1993 |
| gac gaa gac caa cag cac aag gtc acc ttc gac cca acc tcc tcc tac<br>Asp Glu Asp Gln Gln His Lys Val Thr Phe Asp Pro Thr Ser Ser Tyr<br>                     530                           535                          540 | 2041 |
| aca cta gag gac ctg aag cct gac aca ctc tac cgc ttc cag ctg gct<br>Thr Leu Glu Asp Leu Lys Pro Asp Thr Leu Tyr Arg Phe Gln Leu Ala<br>                     545                           550                          555 | 2089 |
| gca cgc tcg gat atg ggg gtg ggc gtc ttc acc ccc acc att gag gcc<br>Ala Arg Ser Asp Met Gly Val Gly Val Phe Thr Pro Thr Ile Glu Ala<br>                560                          565                           570 | 2137 |
| cgc aca gcc cag tcc acc ccc tcc gcc cct ccc cag aag gtg atg tgt<br>Arg Thr Ala Gln Ser Thr Pro Ser Ala Pro Pro Gln Lys Val Met Cys<br>575                            580                        585 | 2185 |
| gtg agc atg ggc tcc acc acg gtc cgg gta agt tgg gtc ccg ccg cct<br>Val Ser Met Gly Ser Thr Thr Val Arg Val Ser Trp Val Pro Pro Pro<br>590                            595                        600                      605 | 2233 |
| gcc gac agc cgc aac ggc gtt atc acc cag tac tcc gtg gcc cac gag<br>Ala Asp Ser Arg Asn Gly Val Ile Thr Gln Tyr Ser Val Ala His Glu<br>                     610                           615                          620 | 2281 |
| gcg gtg gac ggc gag gac cgc ggg cgg cat gtg gtg gat ggc atc agc<br>Ala Val Asp Gly Glu Asp Arg Gly Arg His Val Val Asp Gly Ile Ser<br>                     625                           630                          635 | 2329 |
| cgt gag cac tcc agc tgg gac ctg gtg ggc ctg gag aag tgg acg gag<br>Arg Glu His Ser Ser Trp Asp Leu Val Gly Leu Glu Lys Trp Thr Glu | 2377 |

-continued

```
              640                 645                 650
tac cgg gtg tgg gtg cgg gca cac aca gac gtg ggc ccc ggc ccc gag      2425
Tyr Arg Val Trp Val Arg Ala His Thr Asp Val Gly Pro Gly Pro Glu
    655                 660                 665 agc agc ccg gtg ctg gtg cgc acc gat gag gac gtg ccc agc ggg cct      2473
Ser Ser Pro Val Leu Val Arg Thr Asp Glu Asp Val Pro Ser Gly Pro
670                 675                 680                 685 ccg cgg aag gtg gag gtg gag cca ctg aac tcc act gct gtg cat gtc      2521
Pro Arg Lys Val Glu Val Glu Pro Leu Asn Ser Thr Ala Val His Val
                690                 695                 700 tac tgg aag ctg cct gtc ccc agc aag cag cat ggc cag atc cgc ggc      2569
Tyr Trp Lys Leu Pro Val Pro Ser Lys Gln His Gly Gln Ile Arg Gly
    705                 710                 715 tac cag gtc acc tac gtg cgg ctg gag aat ggc gag ccc cgt gga ctc      2617
Tyr Gln Val Thr Tyr Val Arg Leu Glu Asn Gly Glu Pro Arg Gly Leu
720                 725                 730 ccc atc atc caa gac gtc atg cta gcc gag gcc cag tgg cgg cca gag      2665
Pro Ile Ile Gln Asp Val Met Leu Ala Glu Ala Gln Trp Arg Pro Glu
    735                 740                 745 gag tcc gag gac tat gaa acc act atc agc ggc ctg acc ccg gag acc      2713
Glu Ser Glu Asp Tyr Glu Thr Thr Ile Ser Gly Leu Thr Pro Glu Thr
750                 755                 760                 765 acc tac tcc gtt act gtt gct gcc tat acc acc aag ggg gat ggt gcc      2761
Thr Tyr Ser Val Thr Val Ala Ala Tyr Thr Thr Lys Gly Asp Gly Ala
                770                 775                 780 cgc agc aag ccc aaa att gtc act aca aca ggt gca gtc cca ggc cgg      2809
Arg Ser Lys Pro Lys Ile Val Thr Thr Thr Gly Ala Val Pro Gly Arg
    785                 790                 795 ccc acc atg atg atc agc acc acg gcc atg aac act gcg ctg ctc cag      2857
Pro Thr Met Met Ile Ser Thr Thr Ala Met Asn Thr Ala Leu Leu Gln
800                 805                 810 tgg cac cca ccc aag gaa ctg cct ggc gag ctg ctg ggc tac cgg ctg      2905
Trp His Pro Pro Lys Glu Leu Pro Gly Glu Leu Leu Gly Tyr Arg Leu
    815                 820                 825 cag tac tgc cgg gcc gac gag gcg cgg ccc aac acc ata gat ttc ggc      2953
Gln Tyr Cys Arg Ala Asp Glu Ala Arg Pro Asn Thr Ile Asp Phe Gly
830                 835                 840                 845 aag gat gac cag cac ttc aca gtc acc ggc ctg cac aag ggg acc acc      3001
Lys Asp Asp Gln His Phe Thr Val Thr Gly Leu His Lys Gly Thr Thr
                850                 855                 860 tac atc ttc cgg ctt gct gcc aag aac cgg gct ggc ttg ggt gag gag      3049
Tyr Ile Phe Arg Leu Ala Ala Lys Asn Arg Ala Gly Leu Gly Glu Glu
    865                 870                 875 ttc gag aag gag atc agg acc ccc gag gac ctg ccc agc ggc ttc ccc      3097
Phe Glu Lys Glu Ile Arg Thr Pro Glu Asp Leu Pro Ser Gly Phe Pro
880                 885                 890 caa aac ctg cat gtg aca gga ctg acc acg tct acc aca gaa ctg gcc      3145
Gln Asn Leu His Val Thr Gly Leu Thr Thr Ser Thr Thr Glu Leu Ala
    895                 900                 905 tgg gac ccg cca gtg ctg gcg gag agg aac ggg cgc atc atc agc tac      3193
Trp Asp Pro Pro Val Leu Ala Glu Arg Asn Gly Arg Ile Ile Ser Tyr
910                 915                 920                 925 acc gtg gtg ttc cga gac atc aac agc caa cag gag ctg cag aac atc      3241
Thr Val Val Phe Arg Asp Ile Asn Ser Gln Gln Glu Leu Gln Asn Ile
                930                 935                 940 acg aca gac acc cgc ttt acc ctt act ggc ctc aag cca gac acc act      3289
Thr Thr Asp Thr Arg Phe Thr Leu Thr Gly Leu Lys Pro Asp Thr Thr
    945                 950                 955 tac gac atc aag gtc cgc gca tgg acc agc aaa ggc tct ggc cca ctc      3337
```

```
                Tyr Asp Ile Lys Val Arg Ala Trp Thr Ser Lys Gly Ser Gly Pro Leu
                        960                 965                 970 agc ccc agc atc cag tcc cgg acc atg ccg gtg gag caa gtg ttt gcc         3385
Ser Pro Ser Ile Gln Ser Arg Thr Met Pro Val Glu Gln Val Phe Ala
        975                 980                 985 aag aac ttc cgg gtg gcg gct gca atg aag acg tct gtg ctg ctc agc         3433
Lys Asn Phe Arg Val Ala Ala Ala Met Lys Thr Ser Val Leu Leu Ser
990                 995                 1000                1005 tgg gag gtt ccc gac tcc tat aag tca gct gtg ccc ttt aag att             3478
Trp Glu Val Pro Asp Ser Tyr Lys Ser Ala Val Pro Phe Lys Ile
                1010                1015                1020 ctg tac aat ggg cag agt gtg gag gtg gac ggg cac tcg atg cgg             3523
Leu Tyr Asn Gly Gln Ser Val Glu Val Asp Gly His Ser Met Arg
                1025                1030                1035 aag ctg atc gca gac ctg cag ccc aac aca gag tac tcg ttt gtg             3568
Lys Leu Ile Ala Asp Leu Gln Pro Asn Thr Glu Tyr Ser Phe Val
                1040                1045                1050 ctg atg aac cgt ggc agc agc gca ggg ggc ctg cag cac ctg gtg             3613
Leu Met Asn Arg Gly Ser Ser Ala Gly Gly Leu Gln His Leu Val
                1055                1060                1065 tcc atc cgc aca gcc ccc gac ctc ctg cct cac aag ccg ctg cct             3658
Ser Ile Arg Thr Ala Pro Asp Leu Leu Pro His Lys Pro Leu Pro
                1070                1075                1080 gcc tct gcc tac ata gag gac ggc cgc ttc gat ctc tcc atg ccc             3703
Ala Ser Ala Tyr Ile Glu Asp Gly Arg Phe Asp Leu Ser Met Pro
                1085                1090                1095 cat gtg caa gac ccc tcg ctt gtc agg tgg ttc tac att gtt gtg             3748
His Val Gln Asp Pro Ser Leu Val Arg Trp Phe Tyr Ile Val Val
                1100                1105                1110 gta ccc att gac cgt gtg ggc ggg agc atg ctg acg cca agg tgg             3793
Val Pro Ile Asp Arg Val Gly Gly Ser Met Leu Thr Pro Arg Trp
                1115                1120                1125 agc aca ccc gag gaa ctg gag ctg gac gag ctt cta gaa gcc atc             3838
Ser Thr Pro Glu Glu Leu Glu Leu Asp Glu Leu Leu Glu Ala Ile
                1130                1135                1140 gag caa ggc gga gag gag cag cgg cgg cgg cgg cgg cag gca gaa             3883
Glu Gln Gly Gly Glu Glu Gln Arg Arg Arg Arg Arg Gln Ala Glu
                1145                1150                1155 cgt ctg aag cca tat gtg gct gct caa ctg gat gtg ctc ccg gag             3928
Arg Leu Lys Pro Tyr Val Ala Ala Gln Leu Asp Val Leu Pro Glu
                1160                1165                1170 acc ttt acc ttg ggg gac aag aag aac tac cgg ggc ttc tac aac             3973
Thr Phe Thr Leu Gly Asp Lys Lys Asn Tyr Arg Gly Phe Tyr Asn
                1175                1180                1185 cgg ccc ctg tct ccg gac ttg agc tac cag tgc ttt gtg ctt gcc             4018
Arg Pro Leu Ser Pro Asp Leu Ser Tyr Gln Cys Phe Val Leu Ala
                1190                1195                1200 tcc ttg aag gaa ccc atg gac cag aag cgc tat gcc tcc agc ccc             4063
Ser Leu Lys Glu Pro Met Asp Gln Lys Arg Tyr Ala Ser Ser Pro
                1205                1210                1215 tac tcg gat gag atc gtg gtc cag gtg aca cca gcc cag cag cag             4108
Tyr Ser Asp Glu Ile Val Val Gln Val Thr Pro Ala Gln Gln Gln
                1220                1225                1230 gag gag ccg gag atg ctg tgg gtg acg ggt ccc gtg ctg gca gtc             4153
Glu Glu Pro Glu Met Leu Trp Val Thr Gly Pro Val Leu Ala Val
                1235                1240                1245 atc ctc atc atc ctc att gtc atc gcc atc ctc ttg ttc aaa agg             4198
Ile Leu Ile Ile Leu Ile Val Ile Ala Ile Leu Leu Phe Lys Arg
                1250                1255                1260
```

```
aaa agg acc cac tct  ccg tcc tct aag gat  gag cag tcg atc gga          4243
Lys Arg Thr His Ser  Pro Ser Ser Lys Asp  Glu Gln Ser Ile Gly
            1265                 1270                 1275 ctg aag gac tcc ttg  ctg gcc cac tcc tct  gac cct gtg gag atg          4288
Leu Lys Asp Ser Leu  Leu Ala His Ser Ser  Asp Pro Val Glu Met
            1280                 1285                 1290 cgg agg ctc aac tac  cag acc cca ggt atg  cga gac cac cca ccc          4333
Arg Arg Leu Asn Tyr  Gln Thr Pro Gly Met  Arg Asp His Pro Pro
            1295                 1300                 1305 atc ccc atc acc gac  ctg gcg gac aac atc  gag cgc ctc aaa gcc          4378
Ile Pro Ile Thr Asp  Leu Ala Asp Asn Ile  Glu Arg Leu Lys Ala
            1310                 1315                 1320 aac gat ggc ctc aag  ttc tcc cag gag tat  gag tcc atc gac cct          4423
Asn Asp Gly Leu Lys  Phe Ser Gln Glu Tyr  Glu Ser Ile Asp Pro
            1325                 1330                 1335 gga cag cag ttc acg  tgg gag aat tca aac  ctg gag gtg aac aag          4468
Gly Gln Gln Phe Thr  Trp Glu Asn Ser Asn  Leu Glu Val Asn Lys
            1340                 1345                 1350 ccc aag aac cgc tat  gcg aat gtc atc gcc  tac gac cac tct cga          4513
Pro Lys Asn Arg Tyr  Ala Asn Val Ile Ala  Tyr Asp His Ser Arg
            1355                 1360                 1365 gtc atc ctt acc tct  atc gat ggc gtc ccc  ggg agt gac tac atc          4558
Val Ile Leu Thr Ser  Ile Asp Gly Val Pro  Gly Ser Asp Tyr Ile
            1370                 1375                 1380 aat gcc aac tac atc  gat ggc tac cgc aag  cag aat gcc tac atc          4603
Asn Ala Asn Tyr Ile  Asp Gly Tyr Arg Lys  Gln Asn Ala Tyr Ile
            1385                 1390                 1395 gcc acg cag ggc ccc  ctg ccc gag acc atg  ggc gat ttc tgg aga          4648
Ala Thr Gln Gly Pro  Leu Pro Glu Thr Met  Gly Asp Phe Trp Arg
            1400                 1405                 1410 atg gtg tgg gaa cag  cgc acg gcc act gtg  gtc atg atg aca cgg          4693
Met Val Trp Glu Gln  Arg Thr Ala Thr Val  Val Met Met Thr Arg
            1415                 1420                 1425 ctg gag gag aag tcc  cgg gta aaa tgt gat  cag tac tgg cca gcc          4738
Leu Glu Glu Lys Ser  Arg Val Lys Cys Asp  Gln Tyr Trp Pro Ala
            1430                 1435                 1440 cgt ggc acc gag acc  tgt ggc ctt att cag  gtg acc ctg ttg gac          4783
Arg Gly Thr Glu Thr  Cys Gly Leu Ile Gln  Val Thr Leu Leu Asp
            1445                 1450                 1455 aca gtg gag ctg gcc  aca tac act gtg cgc  acc ttc gca ctc cac          4828
Thr Val Glu Leu Ala  Thr Tyr Thr Val Arg  Thr Phe Ala Leu His
            1460                 1465                 1470 aag agt ggc tcc agt  gag aag cgt gag ctg  cgt cag ttt cag ttc          4873
Lys Ser Gly Ser Ser  Glu Lys Arg Glu Leu  Arg Gln Phe Gln Phe
            1475                 1480                 1485 atg gcc tgg cca gac  cat gga gtt cct gag  tac cca act ccc atc          4918
Met Ala Trp Pro Asp  His Gly Val Pro Glu  Tyr Pro Thr Pro Ile
            1490                 1495                 1500 ctg gcc ttc cta cga  cgg gtc aag gcc tgc  aac ccc cta gac gca          4963
Leu Ala Phe Leu Arg  Arg Val Lys Ala Cys  Asn Pro Leu Asp Ala
            1505                 1510                 1515 ggg ccc atg gtg gtg  cac tgc agc gcg ggc  gtg ggc cgc acc ggc          5008
Gly Pro Met Val Val  His Cys Ser Ala Gly  Val Gly Arg Thr Gly
            1520                 1525                 1530 tgc ttc atc gtg att  gat gcc atg ttg gag  cgg atg aag cac gag          5053
Cys Phe Ile Val Ile  Asp Ala Met Leu Glu  Arg Met Lys His Glu
            1535                 1540                 1545 aag acg gtg gac atc  tat ggc cac gtg acc  tgc atg cga tca cag          5098
Lys Thr Val Asp Ile  Tyr Gly His Val Thr  Cys Met Arg Ser Gln
            1550                 1555                 1560
```

-continued

| | |
|---|---|
| agg aac tac atg gtg cag acg gag gac cag tac gtg ttc atc cat<br>Arg Asn Tyr Met Val Gln Thr Glu Asp Gln Tyr Val Phe Ile His<br>　　　　　　　　1565　　　　　　　　　　　1570　　　　　　　　　　1575 | 5143 |
| gag gcg ctg ctg gag gct gcc acg tgc ggc cac aca gag gtg cct<br>Glu Ala Leu Leu Glu Ala Ala Thr Cys Gly His Thr Glu Val Pro<br>　1580　　　　　　　　　　　1585　　　　　　　　　　1590 | 5188 |
| gcc cgc aac ctg tat gcc cac atc cag aag ctg ggc caa gtg cct<br>Ala Arg Asn Leu Tyr Ala His Ile Gln Lys Leu Gly Gln Val Pro<br>　　　　　　　1595　　　　　　　　　　1600　　　　　　　　　　1605 | 5233 |
| cca ggg gag agt gtg acc gcc atg gag ctc gag ttc aag ttg ctg<br>Pro Gly Glu Ser Val Thr Ala Met Glu Leu Glu Phe Lys Leu Leu<br>　1610　　　　　　　　　　1615　　　　　　　　　　1620 | 5278 |
| gcc agc tcc aag gcc cac acg tcc cgc ttc atc agc gcc aac ctg<br>Ala Ser Ser Lys Ala His Thr Ser Arg Phe Ile Ser Ala Asn Leu<br>　　　　　　　1625　　　　　　　　　　1630　　　　　　　　　　1635 | 5323 |
| ccc tgc aac aag ttc aag aac cgg ctg gtg aac atc atg ccc tac<br>Pro Cys Asn Lys Phe Lys Asn Arg Leu Val Asn Ile Met Pro Tyr<br>　1640　　　　　　　　　　1645　　　　　　　　　　1650 | 5368 |
| gaa ttg acc cgt gtg tgt ctg cag ccc atc cgt ggt gtg gag ggc<br>Glu Leu Thr Arg Val Cys Leu Gln Pro Ile Arg Gly Val Glu Gly<br>　　　　　　　1655　　　　　　　　　　1660　　　　　　　　　　1665 | 5413 |
| tct gac tac atc aat gcc agc ttc ctg gat ggt tat aga cag cag<br>Ser Asp Tyr Ile Asn Ala Ser Phe Leu Asp Gly Tyr Arg Gln Gln<br>　1670　　　　　　　　　　1675　　　　　　　　　　1680 | 5458 |
| aag gcc tac ata gct aca cag ggg cct ctg gca gag agc acc gag<br>Lys Ala Tyr Ile Ala Thr Gln Gly Pro Leu Ala Glu Ser Thr Glu<br>　　　　　　　1685　　　　　　　　　　1690　　　　　　　　　　1695 | 5503 |
| gac ttc tgg cgc atg cta tgg gag cac aat tcc acc atc atc gtc<br>Asp Phe Trp Arg Met Leu Trp Glu His Asn Ser Thr Ile Ile Val<br>　1700　　　　　　　　　　1705　　　　　　　　　　1710 | 5548 |
| atg ctg acc aag ctt cgg gag atg ggc agg gag aaa tgc cac cag<br>Met Leu Thr Lys Leu Arg Glu Met Gly Arg Glu Lys Cys His Gln<br>　　　　　　　1715　　　　　　　　　　1720　　　　　　　　　　1725 | 5593 |
| tac tgg cca gca gag cgc tct gct cgc tac cag tac ttt gtt gtt<br>Tyr Trp Pro Ala Glu Arg Ser Ala Arg Tyr Gln Tyr Phe Val Val<br>　1730　　　　　　　　　　1735　　　　　　　　　　1740 | 5638 |
| gac ccg atg gct gag tac aac atg ccc cag tat atc ctg cgt gag<br>Asp Pro Met Ala Glu Tyr Asn Met Pro Gln Tyr Ile Leu Arg Glu<br>　　　　　　　1745　　　　　　　　　　1750　　　　　　　　　　1755 | 5683 |
| ttc aag gtc acg gat gcc cgg gat ggg cag tca agg aca atc cgg<br>Phe Lys Val Thr Asp Ala Arg Asp Gly Gln Ser Arg Thr Ile Arg<br>　1760　　　　　　　　　　1765　　　　　　　　　　1770 | 5728 |
| cag ttc cag ttc aca gac tgg cca gag cag ggc gtg ccc aag aca<br>Gln Phe Gln Phe Thr Asp Trp Pro Glu Gln Gly Val Pro Lys Thr<br>　　　　　　　1775　　　　　　　　　　1780　　　　　　　　　　1785 | 5773 |
| ggc gag gga ttc att gac ttc atc ggg cag gtg cat aag acc aag<br>Gly Glu Gly Phe Ile Asp Phe Ile Gly Gln Val His Lys Thr Lys<br>　1790　　　　　　　　　　1795　　　　　　　　　　1800 | 5818 |
| gag cag ttt gga cag gat ggg cct atc acg gtg cac tgc agt gct<br>Glu Gln Phe Gly Gln Asp Gly Pro Ile Thr Val His Cys Ser Ala<br>　　　　　　　1805　　　　　　　　　　1810　　　　　　　　　　1815 | 5863 |
| ggc gtg ggc cgc acc ggg gtg ttc atc act ctg agc atc gtc ctg<br>Gly Val Gly Arg Thr Gly Val Phe Ile Thr Leu Ser Ile Val Leu<br>　1820　　　　　　　　　　1825　　　　　　　　　　1830 | 5908 |
| gag cgc atg cgc tat gag ggc gtg gtc gac atg ttt cag acc gtg<br>Glu Arg Met Arg Tyr Glu Gly Val Val Asp Met Phe Gln Thr Val<br>　　　　　　　1835　　　　　　　　　　1840　　　　　　　　　　1845 | 5953 |
| aag acc ctg cgt aca cag cgt cct gcc atg gtg cag aca gag gac<br>Lys Thr Leu Arg Thr Gln Arg Pro Ala Met Val Gln Thr Glu Asp | 5998 |

-continued

```
                  1850                1855                1860
cag tat cag ctg tgc  tac cgt gcg gcc ctg  gag tac ctc ggc agc        6043
Gln Tyr Gln Leu Cys  Tyr Arg Ala Ala Leu  Glu Tyr Leu Gly Ser
                1865                 1870                1875 ttt gac cac tat gca  acg taactaccgc tccctctcc tccgccacc              6091
Phe Asp His Tyr Ala  Thr
                1880 ccgccgtggg gctccggagg ggacccagct cctctgagcc ataccgacca tcgtccagcc    6151 ctcctacgca gatgctgtca ctggcagagc acagcccacg gggatcacag cgtttcagga    6211 acgttgccac accaatcaga gagcctagaa catccctggg caagtggatg gcccagcagg    6271 caggcactgt ggcccttctg tccaccagac ccacctggag cccgcttcaa gctctctgtt    6331 gcgctcccgc atttctcatg cttcttctca tggggtgggg ttggggcaaa gcctcctttt    6391 taatacatta agtggggtag actgagggat tttagcctct tccctctgat ttttcctttc    6451 gcgaatccgt atctgcagaa tgggccactg taggggttgg ggtttatttt gttttgtttt    6511 tttttttttt ttgtatgact tctgctgaag gacagaacat tgccttcctc gtgcagagct    6571 ggggctgcca gcctgagcgg aggctcggcc gtgggccggg aggcagtgct gatccggctg    6631 ctcctccagc ccttcagacg agatcctgtt tcagctaaat gcagggaaac tcaatgtttt    6691 tttaagtttt gttttcccett taaagccttt ttttaggcca cattgacagt ggtgggcggg    6751 gagaagatag ggaacactca tccctggtcg tctatcccag tgtgtgttta acattcacag    6811 cccagaacca cagatgtgtc tgggagagcc tggcaaggca ttcctcatca ccatcgtgtt    6871 tgcaaaggtt aaaacaaaaa caaaaaacca caaaaataaa aaacaaaaaa aacaaaaaac    6931 ccaaaaaaaa aaaaaaaaag agtcagccct tggcttctgc ttcaaaccct caagagggga    6991 agcaactccg tgtgcctggg gttcccgagg gagctgctgg ctgacctggg cccacagagc    7051 ctggctttgg tccccagcat tgcagtatgg tgtggtgttt gtaggctgtg gggtctggct    7111 gtgtggccaa ggtgaatagc acaggttagg gtgtgtgcca cacccatgc acctcagggc     7171 caagcggggg cgtggctggc ctttcaggtc caggccagtg ggcctggtag cacatgtctg    7231 tcctcagagc aggggccaga tgattttcct ccctggtttg cagctgtttt caaagccccc    7291 gataatcgct ctttttccact ccaagatgcc ctcataaacc aatgtggcaa gactactgga   7351 cttctatcaa tggtactcta atcagtcctt attatcccag cttgctgagg ggcagggaga    7411 gcgcctcttc ctctgggcag cgctatctag ataggtaagt gggggcgggg aagggtgcat    7471 agctgtttta gctgagggac gtggtgccga cgtccccaaa cctagctagg ctaagtcaag    7531 atcaacattc cagggttggt aatgttggat gatgaaacat tcattttttac cttgtggatg   7591 ctagtgctgt agagttcact gttgtacaca gtctgttttc tatttgttaa gaaaaactac    7651 agcatcattg cataattctt gatggtaata aatttgaata atcagatttc t             7702
```

What is claimed is:

1. A method for diagnosing thyroid carcinoma, wherein the method comprises steps of:
   obtaining a thyroid tissue specimen from a subject suspected of suffering from thyroid cancer, and
   evaluating immunoreactivity between the tissue specimen and a monoclonal antibody that specifically immunoreacts with a Leukocyte Common Antigen-Related Molecule (LAR) and that distinguishes thyroid carcinoma cells from normal thyroid cells wherein said monoclonal antibody is a secreted product from a hybridoma cell line with Accession No. FERM BP-6343.

* * * * *